United States Patent [19]

Takayanagi et al.

[11] Patent Number: 5,354,874
[45] Date of Patent: Oct. 11, 1994

[54] SUBSTITUTED-ACYCLIC TERPENE COMPOUND

[75] Inventors: Hisao Takayanagi; Yasunori Kitano, both of Yokohama; Yasuhiro Morinaka, Tsuchiura, all of Japan

[73] Assignee: Mitsubishi Kasei Corporation, Tokyo, Japan

[21] Appl. No.: 159,145

[22] Filed: Nov. 30, 1993

Related U.S. Application Data

[60] Division of Ser. No. 44,602, Apr. 9, 1993, Pat. No. 5,304,661, which is a division of Ser. No. 962,016, Oct. 15, 1992, Pat. No. 5,245,085, which is a continuation of Ser. No. 786,071, Oct. 31, 1991, abandoned, which is a continuation-in-part of Ser. No. 730,811, Jul. 25, 1991, abandoned.

[30] Foreign Application Priority Data

Nov. 29, 1989 [JP] Japan .................................. 1-309797
Jun. 20, 1990 [JP] Japan .................................. 2-162439

[51] Int. Cl.$^5$ .................. C07C 69/734; C07D 315/00
[52] U.S. Cl. ...................................... 549/427; 560/183; 560/130; 549/475; 556/445; 556/482
[58] Field of Search ................ 549/427, 475; 560/130, 560/183; 556/445, 482

[56] References Cited

U.S. PATENT DOCUMENTS 4,032,141  6/1977  Hoffmann .
5,166,373  11/1992  Takayanagi et al .
5,245,085  9/1993  Takayanagi et al. .

OTHER PUBLICATIONS

Arfmann et al., Biocatalysis, "Microbial ω-Hydroxylation of trans-Nerolidol and Structurally Related Sesquiterpenoids", vol. 2, pp. 59–67, 1988.
McMurry et al., Tetrahedron Letters, vol. 30, No. 10, pp. 1173–1176 (1989).

*Primary Examiner*—Johann Richter
*Assistant Examiner*—John Peabody
*Attorney, Agent, or Firm*—Wenderoth, Lind & Ponack

[57] ABSTRACT

Acyclic terpene compounds useful as intermediates for producing sarcophytol A which have an anti-carcinogenic promotor activity and anti-tumor activity, which compounds are shown by the general formula (I):

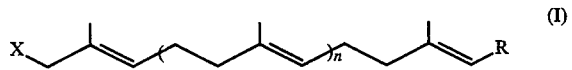

1 Claim, No Drawings

SUBSTITUTED-ACYCLIC TERPENE COMPOUND

CROSS-REFERENCE TO RELATED APPLICATIONS

This application is a division of Ser. No. 08/044,602, filed Apr. 9, 1993, now U.S. Pat. No. 5,304,661 which is a division of Ser. No. 07/962,016, filed Oct. 15, 1992, now U.S. Pat. No. 5,245,085, which is a continuation of Ser. No. 07/786,071, filed Oct. 31, 1991, now abandoned, which is a continuation-in-part of Ser. No. 07/730,811, filed on Jul. 25, 1991, now abandoned, which is the national phase application of International Application No. PCT/JP90/01555, filed on Nov. 29, 1990.

FIELD OF THE ART

The present invention relates to novel substituted-acyclic terpene compounds. More particularly, the present invention is directed to substituted-acyclic terpene compounds useful as intermediates for producing sarcophytol A which have an anti-carcinogenic promotor activity and anti-tumor activity.

BACKGROUND OF THE INVENTION

The sarcophytol A was reported to exhibit anticarcinogenic promotor activity [Cancer Surveys, 2, 540 (1983); Taisha, Vol. 25, Special Edition, Gan '88,3 (1988)] and anti-tumor activity [Japanese Patent Publication 0213/1988], whereby it has been regarded as a useful anti-tumor agent. As can be seen from the following structure, sarcophytol A is a cembrane type diterpene-alcohol containing one conjugated double bond and two other double bonds in the 14-membered ring.

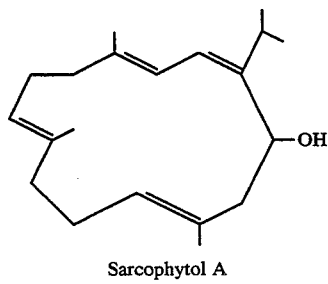

Sarcophytol A

The present inventors studied with the aim of developing a synthetic method of sarcophytol A and proposed a synthetic route shown by the following synthetic route 1 [JP Patent Appln. 181710/1989; filing date: Jul. 14, 1991].

Reaction Route 1

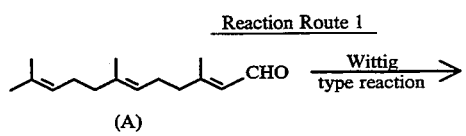

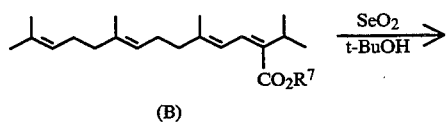

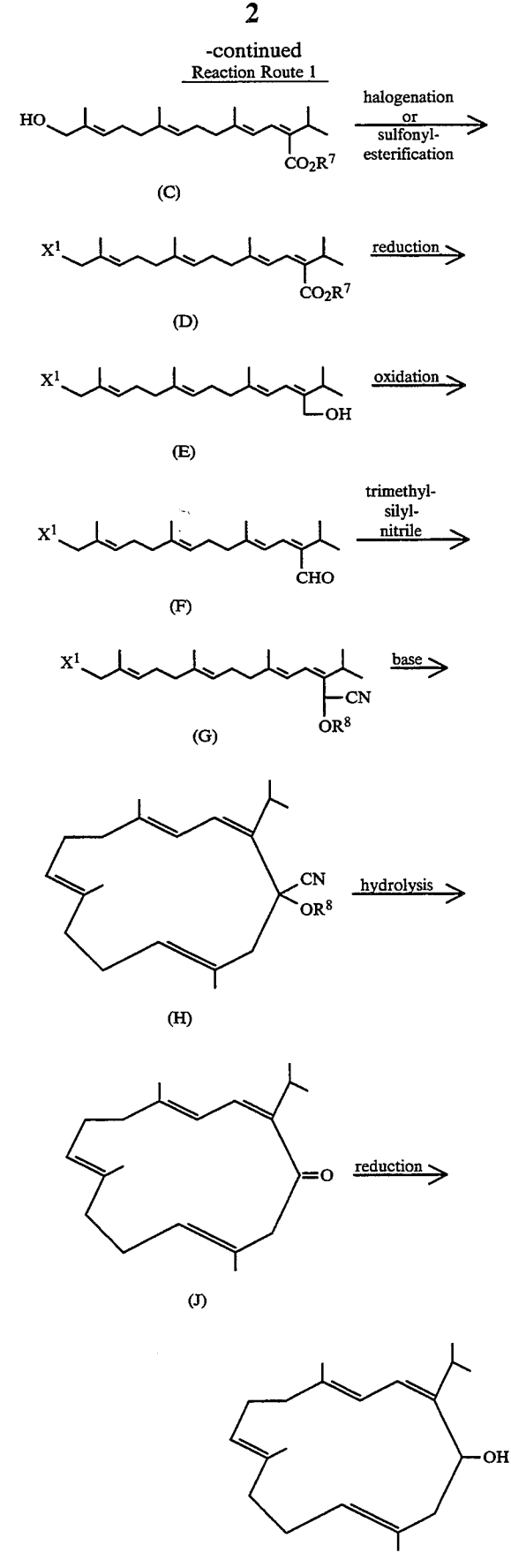

wherein $R^7$ is $C_1$–$C_4$ lower alkyl group or phenyl group; $X^1$ is a halogen atom or a leaving group such as $OSO_2R^9$ and the like; $R^8$ is a hydrogen atom, or trimethylsilyl group or 1-ethoxyethyl group; and $R^9$ is lower alkyl group such as methyl group or ethyl group, substituted alkyl group such as trifluoromethyl group, phenyl group or substituted phenyl group such as toluyl group, mesityl group or the like.

Although the previously proposed method according to the above synthetic route 1 gives the objective sarcophytol A, it has some problems as follows:

1) it requires as the starting material a valuable compound (A), namely "E,E'-farnesol" of a structure essential for the production of sarcophytol A;

2) the oxidation of the terminal methyl group of compound (B) with selenium dioxide is poor in both the selectivity and yield.

3) the process to prepare the Compound (F) by reducing compound (D) to Compound (E), and oxidizing the latter is complicated and inefficient.

Thus, the process shown by the synthetic route 1, especially that concerned with the production of the intermediate (F) from the starting compound (A) is not optimal for the industrial-production of sarcophytol A and a more efficient method for preparing the compound (F) has been demanded.

Under these circumstances, the present inventors have continuously investigated earnestly with the aim of developing a more efficient and simple method for producing the intermediate (F), thereby providing a process applicable to the industrial production of sarcophytol A, and have now found that certain novel substituted-acyclic terpene compounds are useful for the establishment of the purpose of the invention.

DISCLOSURE OF THE INVENTION

The present invention provides acyclic terpene compounds of the general formula (I):

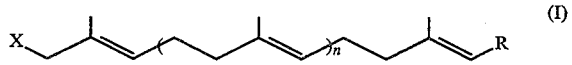

[wherein R is a group of formula:

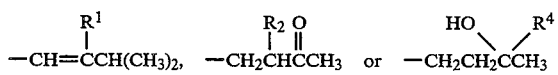

(wherein $R^1$ is cyano group or formyl group; $R^2$ is a hydrogen atom or $-CO_2R^3R$; $R^3$ is $C_1-C_4$ alkyl group; $R^4$ is $-C\equiv CH$ or $-CH=CH_2$); X is a hydrogen atom, a halogen atom, or a group of formula: $-OR^5$ or $-O-SO_2R^6$ (wherein $R^5$ is a hydrogen atom 1-alkoxyalkyl group, tetrahydrofuryl group or tetrahydropyranyl group or silyl group substituted with $C_1-C_5$ alkyl group or phenyl group; $R^6$ is $C_1-C_4$ alkyl group optionally substituted with halogen atom, or phenyl group optionally substituted with $C_1-C_4$ alkyl group); and n is an integer of 0 to 2 with the proviso that when R is a group of formula:

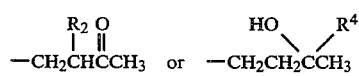

X must be $-OR^5$ and n must be 0; when $R^1$ is formyl group, X is not a halogen atom or $-OSO_2R^6$; when $R^5$ is a hydrogen atom, $R^2$ is not a hydrogen atom; and when $R^5$ is 1-ethoxyethyl group, $R^3$ is not a methyl group].

The terms used for the definition of the compound (I) are explained below.

In the definition of $R^3$, examples of "$C_1$ to $C_4$ lower alkyl group" include a straight or branched alkyl group containing 1 to 4 carbon atoms, for example, methyl group, ethyl group, n-propyl group, isopropyl group, butyl group, isobutyl group, sec-butyl group, tert-butyl group and the like.

In the definition of $R^5$, the term "$C_1$ to $C_5$ lower alkyl group" refers to the above "$C_1$ to $C_4$ lower alkyl group" and pentyl group, isopentyl group, neopentyl group and 1,2-dimethylbutyl group. Examples of "1-alkoxyalkyl group" include methoxymethyl group, 1-ethoxyethyl group and the like. Examples of "silyl group substituted with $C_1-C_5$ alkyl group or phenyl group" include trimethyisilyl group, t-butyldimethylsilyl group, t-butyldiphenylsilyl group and the like. Examples of "acyl group" include acetyl group, propionyl group, benzoyl group and the like.

In the definition of $R^6$ the term "halogen atom" includes fluorine, chlorine, bromine and the like. Examples of "$C_1-C_4$ alkyl group optionally substituted with halogen atom" include methyl group, ethyl group, propyl group, trifluoromethyl group, trichloromethyl group and the like. Examples of "phenyl group optionally substituted with $C_1-C_4$ alkyl group" include phenyl group, p-tolyl group and the like.

PREFERRED EMBODIMENT OF THE INVENTION

Typical compounds represented by the general formula (I) are shown below. However, these are given only for illustrative purpose and never to restrict the scope of the invention.

(1) Compound (I) wherein R is

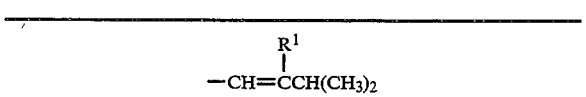

| Compound No. | X |
| --- | --- |
| 1) $R^1 = CN$, n = 0 | |

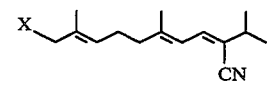

| 1 | —H |
| 2 | —OH |
| 3 | —Cl |
| 4 | $-OSO_2CH_3$ |
| 5 | $-OSO_2-\phenyl-CH_3$ |
| 6 | $-OSi(CH_3)_3$ |
| 7 | 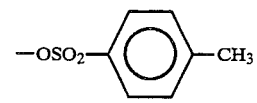 |
| 8 | $-OCHCH_3(O)C_2H_5$ |
| 2) $R^1 = CN$, n = 1 | |

-continued

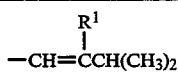

| Compound No. | X |
|---|---|

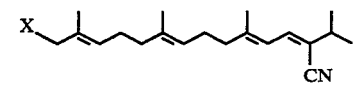

| 9 | —H |
| 10 | —OH |
| 11 | —Cl |
| 12 | —Br |
| 13 | —OSO$_2$CH$_3$ |
| 14 | 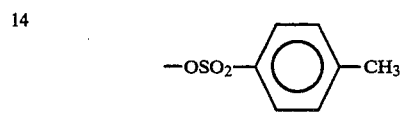 |
| 15 | —OCHCH$_3$(OEt) |
| 16 | —OCH$_2$OCH$_3$ |
| 17 | 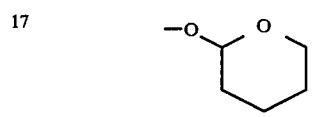 |

3) $R^1$ = CN, n = 2

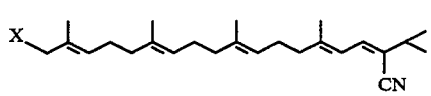

| 18 | —H |
| 19 | —OH |
| 20 | —Cl |
| 21 | —OSO$_2$CH$_3$ |
| 22 | —OCOCH$_3$ |

4) $R^1$ = CHO, n = 0

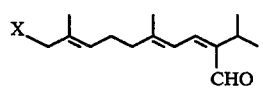

| 23 | —H |
| 24 | —OH |
| 25 | —OSi(CH$_3$)$_2$.C$_4$H$_9$ |
| 26 | —OCHCH$_3$(OC$_2$H$_5$) |
| 27 | 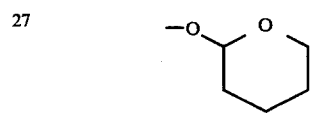 |

5) $R^1$ = CHO, n = 1

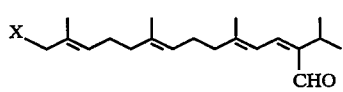

| 28 | —H |
| 29 | —OH |
| 30 | —OCHCH$_3$(OC$_2$H$_5$) |
| 31 | —OCH$_2$OCH$_3$ |
| 32 | 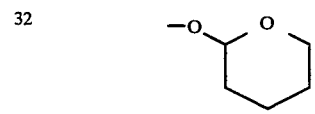 |
| 33 | —OCOCH$_3$ |

-continued

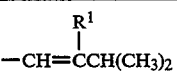

| Compound No. | X |
|---|---|
| 34 | 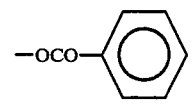 |

6) $R^1$ = CHO n = 2

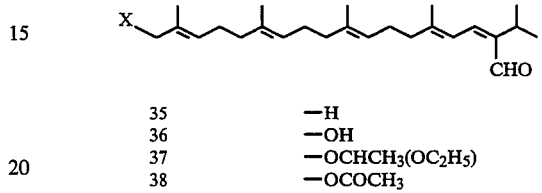

| 35 | —H |
| 36 | —OH |
| 37 | —OCHCH$_3$(OC$_2$H$_5$) |
| 38 | —OCOCH$_3$ |

(2) Compound (I) wherein R is

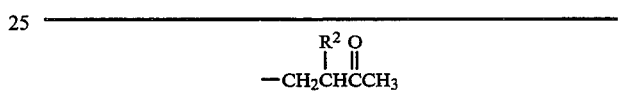

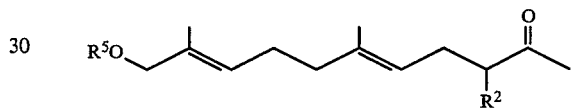

| Compound No. | $R^2$ | $R^5$ |
|---|---|---|
| 1 | —CO$_2$CH$_3$ | —CH$_2$OCH$_3$ |
| 2 | —CO$_2$CH$_3$ | 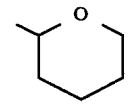 |
| 3 | —CO$_2$CH$_3$ | —Si(CH$_3$)$_2$C$_4$H$_9^t$ |
| 4 | —CO$_2$C$_2$H$_5$ | —Si(CH$_3$)$_2$C$_4$H$_9^t$ |
| 5 | —CO$_2$CH$_3$ | —H |
| 6 | —CO$_2$CH$_3$ | —COCH$_3$ |
| 7 | —CO$_2$CH$_3$ | 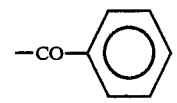 |
| 8 | H | 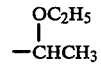 |
| 9 | H | —CH$_2$OCH$_3$ |
| 10 | H | 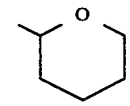 |
| 11 | H | —Si(CH$_3$)$_2$C$_4$H$_9^t$ |
| 12 | H | —COCH$_3$ |
| 14 | H | 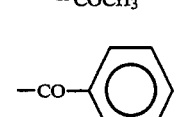 |

(3) Compound (I) wherein R is

| | HO    R⁴ |
|---|---|
| | \\ / |
| | —CH₂CH₂CCH₃ |

R⁵O\~\~\~\~\~\~\~\~\~HO\\R⁴/

| Compound No. | R⁴ | R⁵ |
|---|---|---|
| 15 | —CH=CH₂ | OC₂H₅<br>\|<br>CHCH₃ |
| 16 | —CH=CH₂ | (tetrahydropyranyl-O) |
| 17 | —CH=CH₂ | —CH₂OCH₃ |
| 18 | —CH=CH₂ | —Si(CH₃)₂C₄H₉$^t$ |
| 19 | —CH=CH₂ | —H |
| 20 | —CH=CH₂ | —COCH₃ |
| 21 | —CH=CH₂ | —CO—(phenyl) |
| 22 | —C≡CH | OC₂H₅<br>\|<br>CHCH₃ |
| 23 | —C≡CH | (tetrahydropyranyl-O) |
| 24 | —C≡CH | —CH₂OCH₃ |
| 25 | —C≡CH | —Si(CH₃)₂C₄H₉$^t$ |
| 26 | —C≡CH | —H |
| 27 | —C≡CH | —COCH₃ |
| 28 | —C≡CH | —CO—(phenyl) |

Although all the compounds of the formula (I) including those illustrated in the above are useful as intermediates for the production of sarcophytol A, there are certain preferable compounds, that is, for example, those wherein n is 0 or 1. Especially preferred compounds can be found among the illustrated ones as follows:

(1): compound Nos. 1, 2, 3, 9, 10, 11, 12, 13, 14, 15, 17, 23, 24, 28, 29, 30, 32 and 33; and (2): compounds Nos. 2, 6, 8, 10, 12, 15, 16, 19, 20, 22 and 23.

Preparation of the compound (I) of the present invention is described below according to the type of the directed compound.

(1) Compound of general formula (I) wherein R is a group of formula:

$$-CH=CCH(CH_3)_2$$
with R¹ above the C.

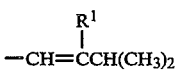

(1) Compounds wherein R¹ is CN and X is H

Among the compounds of this type, those wherein n is 0, 1 or 2 can be prepared from corresponding starting materials, that is, those wherein n is 0 are from geranial, those wherein n is 1 are from farnesol, and those wherein n is 2 are from geranyl geranial, by reacting each starting material with 1 to 10 mol equivalent of Wittig-Horner reagent in the presence of less than 1 mol equivalent of a base (for the Wittig-Horner reagent) in an appropriate solvent.

The Wittig-Horner reagent which can be used is, for example, 2-(dimethylphosphono)isovaleronitrile, 2-(diethylphosphono)isovaleronitrile, or the like. Generally 1 to 10 mol equivalent of such a reagent is used for the starting material.

Examples of appropriate solvents include ether solvents such as tetrahydrofuran (THF), diethyl ether and the like, hydrocarbon solvents such as benzene, toluene, n-hexane and the like and aprotic polar solvents such as dimethylformamide (DMF) and the like. Preferred solvents are hydrocarbon solvents such as toluene, n-hexane and the like.

Examples of bases include metal hydrides such as sodium hydride, potassium hydride and the like, organic metals such as n-butyllithium, lithium diisopropylamide, lithium-bis-(trimethylsilyl)amide, potassium bis-(trimethylsilyl)amide and the like, metal alkoxides such as sodium methoxide, potassium t-butoxide and the like. Generally, less than 1 mol equivalent of such a base is used for the Wittig-Horner reagent. In this reaction, it is possible to control the steric isomerism at the double bond of the product by selecting the solvent and the base.

The reaction is usually carried out at temperature from −100° to 100° C. preferably from −80° to 50° C., more preferably −70° to 0° C.

Each starting compound, when reacted with an anion which is generated during the reaction between the compound and a selected base in the presence of a selected Wittig-Horner reagent at temperature within the cited range in a selected solvent, gives the corresponding product. Under these conditions, the reaction is usually complete in the period from 30 minutes to 12 hours.

2) Compound (I) wherein R¹ is CHO and X is H

Compounds of this type can be prepared, for example, by reacting a compound prepared in above 1) with 1 to 10 mol equivalent of a metal hydride such as diisobutylaluminium hydride at temperature from −100° to 150° C. in a hydrocarbon solvent such as toluene, n-hexane, heptane, benzene or the like, which is followed by hydrolysis.

3) Compounds (i) wherein X is OH

Compounds of this type can be prepared, for example, by reacting a compound prepared in above 1) or 2) with an equivalent amount to 50 mol equivalent of t-butylhydroperoxide in the presence of 0.01 to 0.1 mol equivalent of selenium dioxide at temperature from −20° to 50° C. over a period of 1 to 100 hours in a solvent such as methylenechloride or the like.

4) Compounds (I) wherein R¹ is CN and X is a halogen atom

Compounds of this type can be prepared, for example, from an alcohol wherein R¹ is CN, obtained in above 3), by halogenating said allylic alcohol without allyl rearrangement. Such a reaction can be carried out by reacting the alcohol with 1.0 to 10 mol equivalent of carbon tetrahalide in the presence of 1.0 to 10 mol equivalent of triphenylphosphine at temperature from room temperature to 100° C. over a period of 1 to 8 hours in an inert solvent such as acetonitrile or the like. In case of chlorination, carbon tetrachloride can be used as a solvent. Alternatively, it can be carried out by reacting 1.0 to 10 mol equivalent of methanesulfonyl chloride together with a metal halide and γ-collidine at temperature from −40° C. to room temperature over a period of 1 to 10 hours.

5) Compounds wherein $R^1$ is CN and X is $OSO_2R^6$ ($R^6$ is as defined above)

Compounds of this type can be prepared, for example, by reacting an alcohol wherein $R^1$ is CN obtained in above 3) with 1.0 to 10 mol equivalent of sulfonyl chloride such as methanesulfonyl chloride, p-toluenesulfonyl chloride or sulfonyl anhydride such as trifluoromethanesulfonic anhydride in the presence of 1.0 to 10 mol equivalent of amine such as triethylamine, pyridine or the like at temperature from −40° C. to room temperature over a period of 1 to 10 hours in an ether solvent such as ethyl ether, tetrahydrofuran or the like or a halogen solvent such as methylenechloride, chloroform or the like, or-pyridine in case it is used as a base.

6) Compounds wherein X is $OR^5$ ($R^5$ is as defined above)

a) Compounds wherein $R^5$ is substituted silyl group

Compounds of this type can be prepared by reacting a compound obtained in above 3) with 0.5 to 10 mol equivalent of a substituted silyl chloride such as trimethylchlorosilane, t-butyldimethylchlorosilane or the like in the presence of 0.5 to 10 mol equivalent of a base such as triethylamine, pyridine, imidazole or the like at temperature from −50° to 50 ° C. in an ether solvent such as ethyl ether, THF or the like, an aprotic polar solvent such as dimethylformamide or the like, a halogen solvent such as dichloromethane, chloroform or the like.

b) Compounds wherein $R^5$ is 1-alkoxyalkyl group

Compounds of this type can be prepared by reacting a compound obtained in above 3) with 0.5 to 10 mol equivalent of 1-haloalkyl ether such as chloromethylmethyl ether or chloromethyl-(2-methoxyethyl) ether or the like together with 0.5 to 10 mol equivalent of a base such as sodium hydride, potassium hydride, diisopropylamine, triethylamine or the like at temperature from −50° to 50° in a solvent such as THF, DMF or the like or without solvent; or with 1 to 10 mol equivalent of 1-alkenylalkyl ether such as vinylethyl ether, dihydropyrane or the like in the presence of a catalytic amount to equivalent amount of mineral acid such as hydrochloric acid, sulfuric acid or the like, an organic acid such as p-toluenesulfonic acid, camphorsulfonic acid or the like or a salt such as pyridinium salt of p-toluenesulfonic acid or the like at temperature from −20° to 100 ° C. in an ether solvent such as diethyl ether, THF or the like, an ester solvent such as ethyl acetate or the like, or a halogen solvent such as dichloromethane, chloroform or the like.

c) Compounds wherein $R^5$ is acyl group

Compounds of this type can be prepared by reacting a compound obtained in above 3) with 1 to 10 mol equivalent of acyl halide such as acetyl chloride, benzoyl chloride or the like or acid anhydride such as acetic anhydride, trichloroacetic anhydride or the like in the presence of 1 to 10 mol equivalent of a base such as triethylamine, pyridine or the like at temperature from −20° to 100° C. in a halogen solvent such as dichloromethane, chloroform or the like or an ether solvent such as ethyl ether, THF or the like or a hydrocarbon solvent such as benzene, toluene, n-hexane or the like, or without solvent where a base serves as a solvent.

(2) Compound of general formula group of formula:

1) Compounds (I) wherein $R^5$ is 1-alkoxyalkyl group, tetrahydrofuranyl group or tetrahydropyranyl group, silyl group substituted with $C_1$-$C_5$ alkyl group or phenyl group and $R^2$ is $CO_2R^3$ (wherein $R^3$ is as defined above)

Compounds of this type can be prepared by substituting the hydroxyl group at the 8 position of 8-hydroxygeranyl acetate with $-OR^5$ ($R^5$ is as defined above) according to either of the following methods.

a) 8-Hydroxygeranyl acetate is reacted with 0.1 to 10 mol equivalent of 1-haloalkyl ether such as chloromethylmethyl ether, chloromethyl-2-methoxyethyl ether or the like in the presence of 0.5 to 10 mol equivalent of a base, for example, a metal hydride such as sodium hydride, potassium hydride or the like, amines such as diisopropylamine, triethylamine or the like, or pyridine or the like at temperature from −20° to +100° over a period of 5 minutes to 24 hours in a halogen solvent such as methylene chloride, chloroform or the like, an ether solvent such as diethyl ether, tetrahydrofuran or the like, or ethyl acetate or dimethylformamide or the like, or without solvent.

b) 8-Hydroxygeranyl acetate is reacted with 0.1 to 10 mol equivalent of vinyl ether such as ethylvinyl ether, dihydropyrane or the like in the presence of a catalytic amount to equivalent amount of mineral acid such as hydrochloric acid, sulfuric acid or the like, an organic acid such as p-toluenesulfonic acid, camphorsulfonic acid or the like, or a salt of a strong acid such as pyridinium salt of p-toluenesulfonic acid or the like at temperature from −20° to +100° C. in a halogen solvent such as dichloromethane, chloroform or the like, an ether solvent such as diethyl ether, tetrahydrofuran or the like, or ethyl acetate or dimethylformamide or the like, or without solvent.

c) 8-Hydroxygeranyl acetate is reacted with 0.1 to 10 mol equivalent of trialkylsilyl halide such as trimethylsilyl chloride, t-butyldimethylsilyl chloride or the like in the presence of 0.1 to 10 mol equivalent of a base such as nitrogen-containing compound such as triethylamine, dimethylaminopyridine, imidazole or the like, or metal hydride such as sodium hydride, potassium hydride or the like at temperature from −20° to +100 ° C. over a period of 5 minutes to 24 hours in a halogen solvent such as methylene chloride, chloroform or the like, a hydrocarbon solvent such as hexane, benzene or the like, an ether solvent such as diethyl ether, tetrahydrofuran or the like, or ethyl acetate, dimethylformamide, dimethyl sulfoxide or the like.

The resultant compound, when reacted, for example, with an alkali metal salt of acetoacetic ester, gives the desired compound. Thus, the compound is reacted with an alkali metal salt of an acetoacetic ester at temperature from −70° to +100° C. over a period of 30 minutes to 48 hours in an aprotic polar solvent such as diethyl ether, tetrahydrofuran, dimethylformamide, dimethyl sulfoxide or the like to give the directed compound, Where the alkali metal salt of an acetoacetic ester can be prepared by reacting an acetoacetic ester such as ethyl acetoacetate, ethyl acetoacetate or the like with a metal hydride such as sodium hydride or the like, or a strong base such as n-butyllithium, lithium diisopropylamine or the like in the presence of a palladium (0) chelate such as tetrakis(triphenylphosphine) palladium and the like as a catalyst at temperature from −70° to +100° C. in an aprotic polar solvent such as diethyl ether, tetrahydrofuran, dimethylformamide, dimethyl sulfoxide or the like.

2) Compounds (I) wherein $R^5$ is H and $R^2$ is $CO_2R^3$ ($R^3$ is as defined above)

Compounds of this type can be prepared by reacting a compound obtained in above 1) with 0.1 to 10 mol equivalent of a mineral acid such as hydrochloric acid, sulfuric acid or the like, an organic strong acid such as p-toluenesulfonic acid or the like or a salt of a strong acid such as pyridinium salt of p-toluenesulfonic acid or the like in an alcohol solvent such as methanol, ethanol or a the like or water, or a mixed solvent thereof. Alternatively, it can be prepared by reacting the compound obtained in 1) with 0.1 to 10 mol equivalent of tetraalkylammonium fluoride such as tetrabutylammonium fluoride or hydrogen fluoride in a protonic polar solvent such as methanol, ethanol, water or the like, an ether solvent as diethyl ether, tetrahydrofuran or the like, or a mixed solvent thereof.

3) Compounds (I) wherein $R^5$ is acyl group and $R^2$ is $CO_2R^3$ ($R^3$ is as defined above)

Compounds of this type can be prepared by reacting a compound obtained in above 2) with 0.1 to 10 mol equivalent of acyl halide such as acetyl chloride, benzoyl chloride or the like or acid anhydride such as acetic anhydride or the like in the presence of 0.1 to 10 mol equivalent of a base such as triethylamine, pyridine or the like at temperature from −20° to +100° C. in a halogen solvent such as dichloromethane or the like, an ether solvent such as diethyl ether or the like, a hydrocarbon solvent such as benzene, n-hexane or the like, or without solvent where a base serves as a solvent.

4) Compounds (I) wherein $R^5$ is a hydrogen atom, 1-alkoxyalkyl group, tetrahydrofuranyl group, tetrahydropyranyl group, silyl group substituted with $C_1-C_5$ alkyl group or phenyl group or acyl group and $R^2$ is a hydrogen atom Compounds of this type can be prepared through the decarboxylation or decarboalkoxylation of a compound obtained in above 1), 2) or 3). The decarboxylation can be carried out by reacting said compound with 0.1 to 10 mol equivalent of a metal hydroxide such as sodium hydroxide, potassium hydroxide or the like, metal alkoxide such as sodium methoxide or the like at temperature from 0° to 100° C. over a period of 10 minutes to 24 hours for the hydrolysis or ester-exchanging reaction, and heating at temperature from 100° to 250° C. over a period of 30 minutes to 10 hours. The decarboalkoxylation which is carried out by reacting a compound with 0.1 to 10 mol equivalent of a metal halide such as sodium chloride, sodium iodide or the like at temperature from 50° to 250° C. in an aprotic polar solvent such as dimethylformamide, dimethylsulfoxide or the like.

(3) Compounds (I) wherein R is a group of formula:

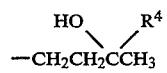

1) Compounds (I) wherein $R^5$ is a hydrogen atom, 1-alkoxyalkyl, tetrahydrofuranyl or tetrahydropyranyl group, or silyl group substituted with $C_1-C_5$ alkyl group or phenyl group and $R^4$ is —CH=$CH_2$ Compounds of this type can be prepared by subjecting a compound obtained in (2), 4) to an addition reaction, which is conducted by reacting said compound with 0.1 to 10 mol equivalent of a vinyl anion such as vinyl lithium, vinyl magnesium bromide or the like at temperature from −50° to 100° C. over a period of 30 minutes to 48 hours in an ether solvent such as diethyl ether, tetrahydrofuran or the like or a hydrocarbon solvent such as n-hexane, benzene or the like.

2) Compounds (I) wherein $R^5$ is a hydrogen atom, 1-alkoxyalkyl group, tetrahydrofuranyl group, tetrahydropyranyl group or silyl group substituted with $C_1-C_5$ alkyl group or phenyl and $R^4$ is —C≡CH Compounds of this type can be prepared by subjecting a compound obtained in above (2), 4) to an addition reaction which is conducted by reacting said compound with 0.1 to 10 mol equivalent of a metal acetylide such as lithium acetylide, ethynyl magnesium bromide or the like at temperature from −50° to +100° C. over a period of 30 minutes to 48 hours in an ether solvent such as diethyl ether, tetrahydrofuran or the like or a hydrocarbon solvent such as n-hexane, benzene or the like.

3) Compounds (I) wherein $R^5$ is acyl group and $R^4$ is a group of —CH=$CH_2$ or —C≡CH.

Compounds of this type can be prepared by reacting a compound obtained in above (3),1) or 2), in which $R^5$ is a hydrogen atom and $R^4$ is —CH=$CH_2$ or —C≡CH, with 0.1 to 10 mol equivalent of acyl halide such as acetyl chloride, benzoyl chloride or the like or acid anhydride such as acetic anhydride or the like in the presence of 0.1 to 10 mol equivalent of a base such as triethylamine, pyridine or the like at temperature from −20° to +100° C. in a halogen solvent such as dichloromethane or the like, an ether solvent such as diethyl ether or the like, a hydrocarbon solvent such as benzene, n-hexane or the like, or without solvent where a base serves as a solvent.

The above are examples of preferred procedures for the production of the compounds of formula (I) of the invention. As one of skill in the art will appreciate, the present invention is not restricted to the compounds (I) produced by the above methods, but includes any compounds of formula (I) prepared by other methods known to the art.

As mentioned above, the present invention makes it possible to obtain Compound (F), the key intermediate in the synthetic route 1 for the production of sarcophytol A, from a monoterpenoid which is cheap and easy to obtain, by an improved and efficient process with avoiding the oxidation of alcohol to aldehyde of the previously provided method, reducing the total steps, and in high yield.

Thus, the present invention provides an industrially advantageous synthetic route for preparing sarcophytol A.

Typical procedures for the production of the intermediate (F) in the synthetic route 1 from various compounds (I) of the invention as the starting material, and that for the production of the final product, sarcophytol A, will hereinafter be described.

(1) When the starting material is a compound (I) wherein X is a halogen atom, n is 1 and R is a group of formula:

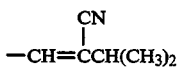

Compound (F) in the above synthetic route 1 can be prepared by reacting a compound (I) as defined above with 0.1 to 10 mol equivalent of diisobutylaluminium hydride in a solvent such as toluene, benzene, n-hexane or the like at temperature from −100° to 100 ° C. and hydrolyzing the product.

When the starting material is Compound (I') which is shown by the formula (I) wherein $R^5$ is 1-alkoxyalkyl group and R is a group of formula:

or Compound (I'') which is shown by the formula (I) wherein $R^2$ is 1-alkoxyalkyl group and R is a group of formula:

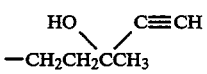

carbon solvent such as undecane, xylene or the like, an ether solvent such as bis[2-(2-methoxyethoxy)-ethyl]ether or a mineral oil.

b) When the starting material is Compound (I'')

An unsaturated aldehyde (A') can be prepared by reacting the Compound (I'') with chromic oxides such as pyridinium chlorochromate or the like at temperature from 0° to 100° C. over a period of 30 minutes to 24 hours in a halogen solvent such as methylene chloride, chloroform or the like, a hydrocarbon solvent such as n-hexane, benzene or the like, or dimethylformamide or the like.

c) Compound (B') can be prepared by reacting Compound (A') with 0.1 to 10 mol equivalent of Wittig-Horner reagent such as 2-(dimthylphosphono)isovaleronitrile, 2-(diethylphosphono)isovaleronitrile or the like in an ether solvent such as tetrahydrofuran, diethyl ether or the like, a hydrocarbon solvent such as toluene, n-hexane or the like or an aprotic polar solvent such as dimethylformamide, dimethyl sulfoxide or the like at temperature from −100° to +100° C., in the presence of less than 1 mol equivalent (for the Wittig-Horner reagent) of a base, for example, metal hydride such as sodium hydride, potassium hydride or the like, organic metal (e.g. n-butyllithium, lithium diisopropylamide) or metal alkoxide such as sodium methoxide, potassium t-butoxide

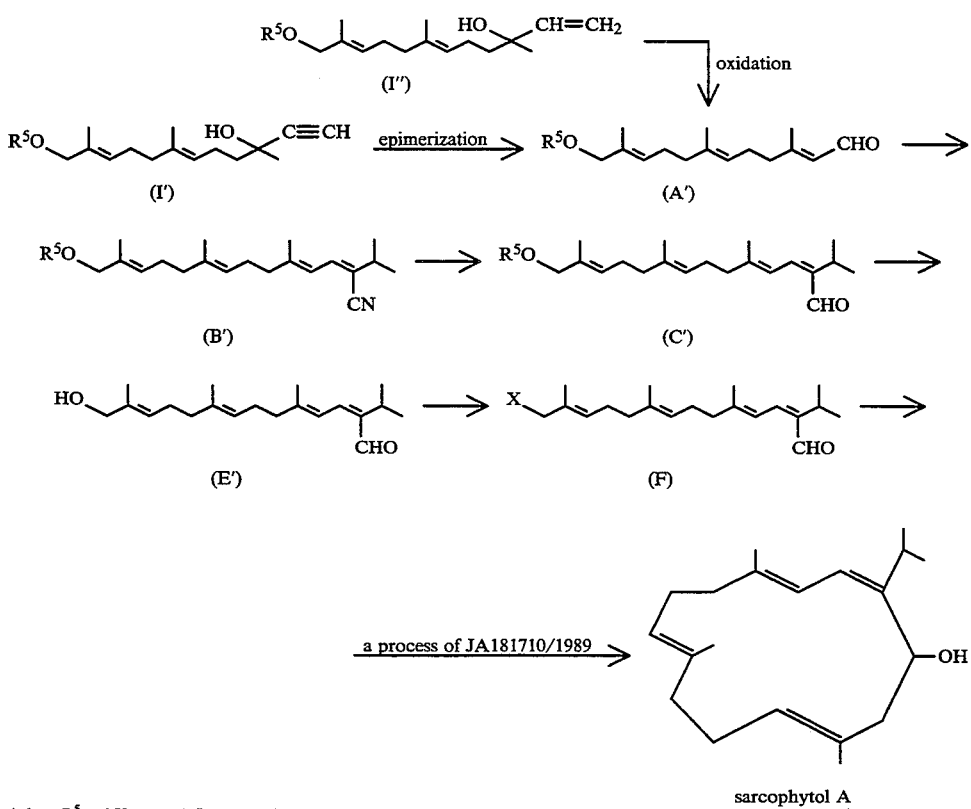

(where $R^5$ and X are as defined above).

a) When the starting material is Compound (I')

Compound (A') can be prepared by subjecting the Compound (I') to rearrangement reaction in the presence of 0.01 to 1 mol equivalent of silylvanadate such as tris(triphenylsilyl)vanadate, poly{(diphenylsilyl)-vanadate} or the like at temperature from 100° to 300° C. over a period of 30 minutes to 24 hours in a hydroor the like while allowing Compound (A') to react with a generated anion.

Aldehyde (C') is prepared by reacting Compound (B') with 0.1 to 10 mol equivalent of a metal hydride complex such as lithium aluminum hydride or the like at temperature from −70° to +100° C. in an ether solvent such as diethyl ether, tetrahydrofuran or the like or reacting with 0.1 to 10 mol equivalent of a metal hydride such as diisobutylaluminium hydride or the like at temperature from −70° to +100° C. over a period of 5 minutes to 5 hours in a hydrocarbon solvent such as n-hexane, benzene or the like.

Aldehyde (C') is converted into alcohol (E') when treated with 0.1 to 10 mol equivalent of a mineral acid such as hydrochloric acid, sulfuric acid or the like, an organic strong acid such as p-toluenesulfonic acid or a salt of a strong acid such as a pyridinium salt of p-toluenesulfonic acid or the like in a solvent such as aqueous methanol, aqueous ethanol, aqueous tetrahydrofuran, or a mixed solvent thereof.

Compound (F) can be prepared from Compound (E') by halogenating the allylic alcoholic without allyl rearrangement. For example, Compound (E') is reacted with 0.1 to 10 mol equivalent of carbon tetrahalide in the presence of 1.0 to 10 mol equivalent of triphenylphosphine in a solvent such as acetonitrile, dichloromethane or the like, in case of chlorination, with carbon tetrachloride without solvent, at temperature from −10° to +100° C. over a period of 10 minutes to 12 hours. Alternatively, Compound (E') is reacted with 0.1 to 10 mol equivalent of sulfonyl halide such as methanesulfonyl chloride, p-toluenesulfonyl chloride or the like together with a metal halide such as lithium chloride in the presence of an amine such as pyridine, γ-collidine, lutidine or the like at temperature from −40° to +30° C. over a period of 1 to 12 hours.

The final product, sarcophytol A, can be prepared be treating Compound (F) according to the procedure shown by the synthetic route 1 as shown below.

PROCESS OF THE SYNTHETIC ROUTE 1 a) Preparation of Compound (G)

Thus, Compound (G) wherein $R^8$ is trimethylsilyl group is prepared, for example, by treating Compound (F) with 1.0 to 10 mol equivalent of trimethylsilylnitrile in the presence of a catalytic amount of metal cyanide 18-crown-6-ether complex, an ammonium salt such as tetraalkylammonium cyanide or the like at temperature from −20° to 50° C. over a period of 30 minutes to 5 hours in a solvent such as methylene chloride, chloroform, ethyl acetate or the like, or without solvent. The resultant product can be converted into cyanohydrin wherein $R^8$ is hydrogen by treating with 0.1-3N aqueous mineral acid such as hydrochloric acid, sulfuric acid or the like at 0° C. to room temperature over a period of 5 minutes to 5 hours or by treating with a catalytic amount to 10 mol equivalent of tetraalkylammonium salt such as tetrabutylammonium fluoride or the like at temperature from −20° C. to room temperature in a solvent such as tetrahydrofuran, dioxane or the like.

Compound (G) wherein $R^8$ is 1-ethoxyethyl group can be prepared by reacting the above cyanohydrin with t.0 to 10 mol equivalent of ethyl vinyl ether in the presence of a catalytic amount of mineral acid such as hydrochloric acid, sulfuric acid or the like, an organic strong acid such as p-toluenesulfonic acid or the like, or a salt of strong acid such as p-toluenesulfonic acid or the like pyridinium salt at temperature from −20° C. to room temperature over a period of 30 minutes to 5 hours in a solvent such as ethyl ether, ethyl acetate or the like.

b) Preparation of Compound (H)

Compound (H) wherein $R^8$ is trimethylsilyl or 1-ethoxyethyl group can be prepared by reacting Compound (G) wherein $R^8$ is trimethylsilyl group or 1-ethoxyethyl group with 1.0 to 10 mol equivalent of a base such as lithium diisopropylamide, lithium bis-(trimethylsilyl) amide, sodium hydride or the like at temperature from −70° to 100° C. over a period of 5 minutes to 10 hours in an ether solvent such as ethyl ether, tetrahydrofuran or the like, an aromatic hydrocarbon solvent such as benzene, toluene or the like or a saturated hydrocarbon solvent such as n-hexane, n-heptane or the like.

Compound (H) wherein $R^8$ is a hydrogen atom is prepared by treating the compound obtained above with 0.1-3N aqueous mineral acid such as hydrochloric acid, sulfuric acid or the like at temperature from 0° C. to room temperature over a period of 5 minutes to 5 hours in a solvent such as tetrahydrofuran, methanol or the like or by treating with a catalytic amount to 10 mol equivalent of tetraalkylammonium salt such as tetrabutylammonium fluoride at temperature from −20° C. to room temperature in a solvent such as tetrahydrofuran, dioxane or the like.

c) Preparation of a Ketone, Compound (J)

The ketone (J) can be prepared by treating a solution of Compound (H) wherein $R^8$ is a hydrogen atom in an organic solvent such as ethyl ether, ethyl acetate or the like with aqueous sodium bicarbonate at temperature from 0° C. to room temperature over a period of 5 minutes to 5 hours, or by treating Compound H wherein $R^8$ is trimethylsilyl group with a catalytic amount to 10 mol equivalent of an alkylammonium fluoride such as tetrabutylammonium fluoride in a solvent such as aqueous tetrahydrofuran, dioxane or the like.

d) Preparation of Sarcophytol A

Sarcophytol A can be prepared by reacting the ketone (J) thus obtained with 1.0 to 10 mol equivalent of a metal hydride such as diisobutylaluminum hydride or the like or a metal complex such as lithium aluminum hydride or the like at temperature from −70° to 50° C. over a period of 5 minutes to 5 hours in an ether solvent such as ethyl ether, tetrahydrofuran or the like, an aromatic hydrocarbon solvent such as benzene, toluene or the like or a saturated hydrocarbon solvent such as n-hexane, n-heptane or the like.

Further, sarcophytol A in native form shown below is prepared by subjecting ketone Compound (J) to asymmetric reduction with an asymmetrically-modified metal hydride or metal hydride complex.

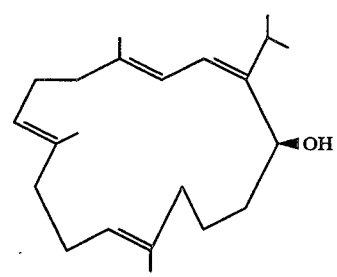

Sarcophytol A in native form

Sarcophytol A in native form

Examples of asymmetrically-modifying reagents used for preparing asymmetrically-modified metal hydride or metal hydride complex, which are used in the asymmetric reduction, include asymmetric amino alcohols prepared by converting carboxy group of optically-active amino acid such as L- or D-proline, valine or the like into substituted alcohol group or substituted amino group [Bull. Soc. Chim. Belg. 97:691 (1988); J. Chem. Soc. Perkin I 1673: (1983)]; asymmetric diamines [Bull. Chem. Soc. Japan 51:1869 (1978); Tetrahedron 37:4111 (1981)], asymmetric alkaloids such as L- or D-methylephedrine and the like [Chem. Pharm. Bull. 31:837 (1983)]; and (S)- or (R)-1,1'-bis-2-naphtol and the like.

Examples of metal hydrides or metal hydride complexes include diisobutylaluminium hydride, lithium aluminium hydride, sodium borohydride and the like. An asymmetric reducing reagent can be prepared by reacting a metal hydride or metal hydride complex with 0.1 to 5 mol equivalent, preferably 0.5 to 1.5 mol equivalent of the above-mentioned asymmetrically-modifying reagent, optionally in the presence of an additive such as alkyl-substituted aniline, substituted aminopyridine, stannous chloride or the like at temperature from $-50°$ to $50°$ C., preferably from $-20°$ C. to room temperature over a period of 10 minutes to 5 hours in an appropriate solvent to obtain a coordinated complex of said asymmetrically-modifying reagent and metal hydride or metal hydride complex. Examples of appropriate solvents include ether solvents such as diethyl ether, tetrahydrofuran and the like and hydrocarbon solvents such as benzene, toluene, n-hexane and the like. A halogen solvent such as dichloromethane and chloroform is also available in case metal hydride is used. Illustrative combinations are listed in the Table 1 below.

TABLE 1

| metal hydride or metal hydride complex | asymmetric modifying reagent | additive |
|---|---|---|
| LiAlH$_4$ | [structure: Ph-CH(OH)-CH(NMe$_2$)-Me] | [structure: H$_5$C$_2$N(H)-phenyl] |
| LiAlH$_4$ | [pyrrolidine-CH(NH-phenyl)] | — |
| LiAlH$_4$ | [pyrrolidine-CH(NH-(2,6-dimethylphenyl))] | — |
| HAl(i-Bu)$_2$ (DIBAL) | [N-Me pyrrolidine-CH=N-piperidine] | SnCl$_2$ |

TABLE 1-continued

| metal hydride or metal hydride complex | asymmetric modifying reagent | additive |
|---|---|---|
| BH$_3$ | [pyrrolidine-C(Ph)(Ph)-O-B(Me)-N] | — |
| BH$_3$ | [iPr-CH(NH)-C(Ph)(Ph)-O-B(H)] | — |

Although the amount of the asymmetric reducing reagent to be reacted with the macrocyclic ketone shown by the structure (J) is not critical, it is preferable to use 1 to 2 mol equivalent of asymmetric reducing reagent for the ketone considering the recovery of unreacted starting materials and yield of the product. The reaction is usually conducted at temperature from $-150°$ to $100°$ C., preferably from $-100°$ C. to room temperature over a period of 10 minutes to 5 hours in the same solvent as that used for the preparation of the asymmetric reducing reagent. No regularity can be found between the absolute configuration of the product sarcophytol A ( its native form is expressed by I$_R$ and non-native form I$_S$ as shown below) and that of the asymmetric reducing reagent, which is attributable to the original compound in L- or D-form. The absolute configuration of the product varies depending on the combination of the asymmetric reducing reagent and metal hydride or metal hydride complex.

The by-product of the present method, sarcophytol A in non-native form of formula:

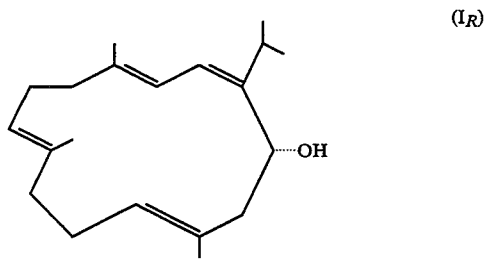

(I$_R$)

when subjected to the conventional epimerization reaction for hydroxyl group, easily gives the optically-active sarcophytol A (I$_S$) in native form after the inversion.

(3) When the starting material is a compound of formula (I) wherein n is 1 and R is a group of formula:

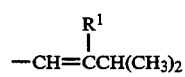

wherein R$^1$ is as defined above.

Synthetic Route 3

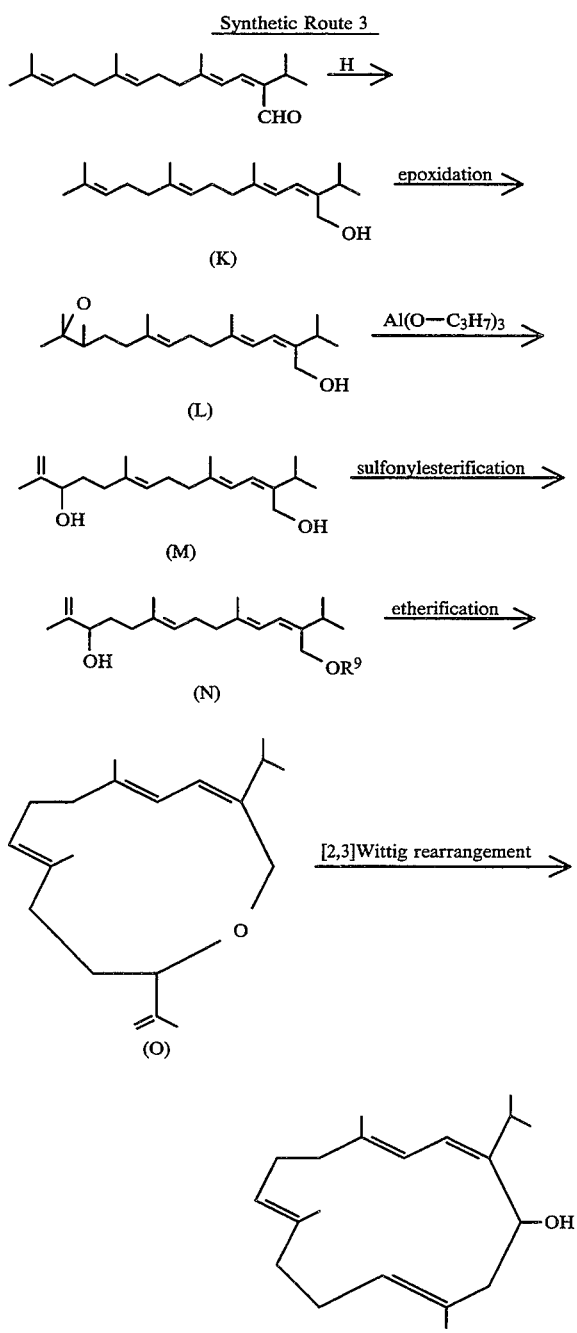

sarcophytol A

R[9]: substituted sulfonyl group such as methanesulfonyl group or p-toluenesulfonyl group.

Compound (K) in the above synthetic route 3 can be prepared by, for example, reacting a compound of formula (I) wherein n is 1, X is a hydrogen atom and R is a group:

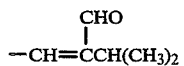

with either of 1.0 to 10 tool equivalent of metal hydride such as dibutylaluminium hydride or the like, or a metal complex such as lithium aluminium hydride or the like at temperature from −70° to 50 ° C. over a period of 5 minutes to hours in a ether solvent such as ethyl ether, tetrahydrofuran or the like, an aromatic hydrocarbon solvent such as benzene, toluene or the like or a saturated hydrocarbon solvent such as n-hexane, n-heptane or the like; or with 0..5 to 10 mol equivalent of metal hydride complex such as sodium borohydride or the like at temperature −70° to 100° C. in a solvent such as methanol, ethanol or the like.

The resulting Compound (K) is converted into Compound (L) through the epoxidation which is conducted by halogenating the Compound K with 0.1 to 1 mol equivalent of a halogenating agent such as N-bromosuccinimide, N-chlorosuccinimide or the like at temperature from −20° to 100° C. over a period of 30 minutes to 5 hours in an aqueous solvent of a water-miscible solvent such tetrahydrofuran, dimethoxyethane or the like, followed by treating with an aqueous solution of a base such as sodium hydroxide, potassium hydroxide, sodium carbonate or the like, or after the halogenation, isolating halohydrin, and treating it with a base such as sodium carbonate, sodium methoxide or the like in a solvent such as methanol or tetrahydrofuran or the like; or by treating with 0.1 to 1 mol equivalent of organic peracid such as m-chloroperbenzoic acid, peracetic acid or the like at temperature from −50° to 50° C. over a period of 30 minutes to 10 hours.

Compound (M) can be prepared by reacting Compound (L) with 0.1 to 10 mol equivalent of metal alkoxide such as aluminium triisopropoxide or the like at temperature from 50° to 200° C. in a solvent such as toluene, xylene or the like; or with 0.1 to 10 mol equivalent of a metal amide such as lithium diisopropylamide, lithium diethylamide or the like at temperature from −70° to 100 ° C. in a solvent such as diethyl ether, tetrahydrofuran or the like.

Compound (N) can be prepared by the sulfonylesterification of the diallyl alcohol (M). For example, Compound (M) is reacted with 0.1 to 1.5 mol equivalent of a substituted sulfonyl chloride such as methanesulfonyl chloride, p-toluenesulfonyl chloride or the like in the presence of 0.1 to 10 mol equivalent of a base such as triethylamine, pyridine or the like at temperature from −70° to 100 ° C. in a halogen solvent such as dichloromethane, chloroform or the like or a ether solvent such as diethyl ether, tetrahydrofuran or the like.

Compound (O) can be prepared, for example, by treating Compound (N) with 0.1 to 10 mol equivalent of metal hydride such as sodium hydride, potassium hydride or the like or organic metal such as n-butyllithium, ethyl magnesium chloride or the like at temperature from −50° to 150 ° C. in an ether solvent such as diethyl ether, tetrahydrofuran or the like, a hydrocarbon solvent such as benzene, toluene, n-hexane or the like or an aprotonic polar solvent such as dimethylformamide, dimethyl sulfoxide or the like.

The resultant Compound (O) can be converted into sarcophytol A by reacting said Compound (O) with 0.1 to 10 mol equivalent of organic metal such as n-butyl lithium, sec-butyl lithium, lithium diisopropyl amide or the like at temperature from −100° to 100 ° C. in an ether solvent such as diethyl ether, tetrahydrofuran or the like, a hydrocarbon solvent such as benzene, toluene, n-hexane or the like, or further adding hexamethylphosphoric triamide or the like to the solvent.

(4) When the starting material is a compound of formula I wherein n is 0 and R is a group of formula:

$$-\overset{R^1}{\underset{|}{CH}}=CCH(CH_3)_2$$

wherein $R^1$ is as defined above.

Synthetic route 4

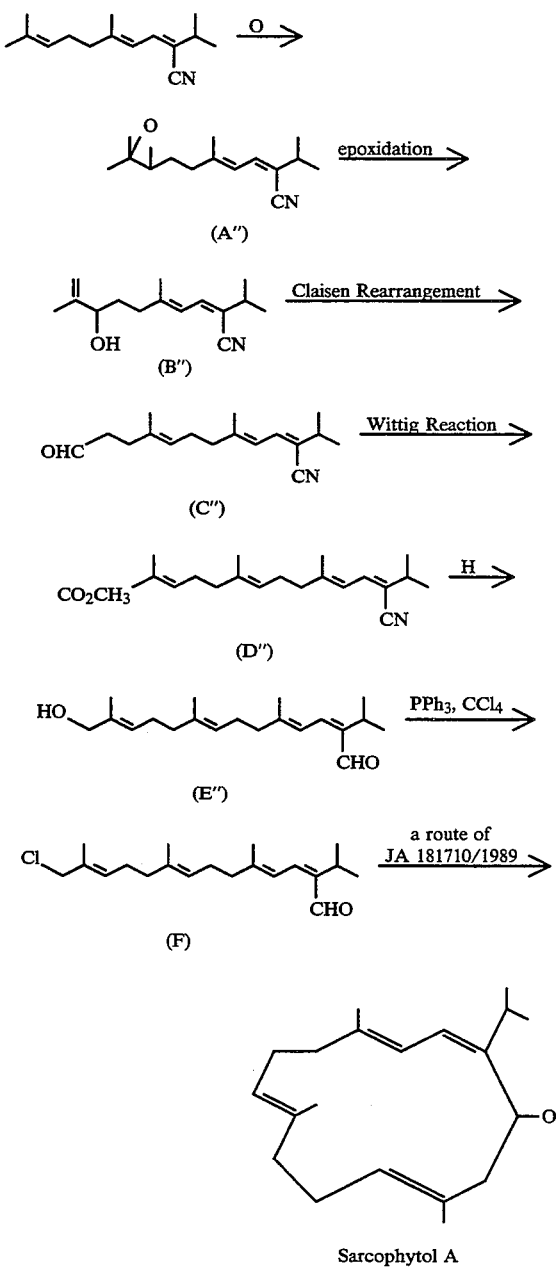

Sarcophytol A

Compound (A″) in the above synthetic route 4 can be prepared from a compound (I) wherein $R^1$ is —CN, n is 0 and X is a hydrogen atom as mentioned above through epoxidation as follows. Thus, Compound (A″) is prepared by halogenating a compound (I) with 0.1 to 1 mol equivalent of a halogenating agent such as N-bromosuccinimide, N-chlorosuccinimide or the like at temperature from —50° to 50° C. over a period of 30 minutes to 5 hours in an aqueous solvent of a water-miscible solvent such tetrahydrofuran, dimethoxyethane or the like, followed by treating with an aqueous solution of a base such as sodium hydroxide, potassium hydroxide, sodium carbonate or the like, or after the halogenation, separating halohydrine, and reducing it with a base such as sodium carbonate, sodium methoxide or the like in a solvent such as methanol or tetrahydrofuran or the like; or by treating the compound with 0.1 to 1 mol equivalent of organic peracid such as m-chloroperbenzoic acid, peracetic acid or the like at temperature from —50° to 50° C. over a period of 30 minutes to 10 hours.

Compound (B″) is prepared by treating the above epoxy compound (A″) with 0.1 to 10 mol equivalent of metal alkoxide such as aluminium triisopropoxide or the like at temperature from 50° to 200 ° C. in a solvent such as toluene, xylene or the like; or with 0.1 to 10 mol equivalent of a metal amide such as lithium diisopropylamide, lithium diethylamide or the like at temperature from —70° to 100° C. in a solvent such as diethyl ether, tetrahydrofuran or the like.

The aldehyde compound (C″) can be prepared by, for example, through the Claisen rearrangement, which is conducted by reacting Compound (B″) with 1.0 to 100 mol equivalent of alkyl vinyl ether such as ethyl vinyl ether or the like in the presence of 0.1 to 5 mol equivalent of a mercury salt such as mercury acetate or the like at temperature from to 100° C. to give the vinyl ether of Compound (B″) or leading said Compound (B″) to 3-alkoxyacrylic acid according to a known method [*J. Org. Chem.*, 48:5406 (1983)], followed by heating at temperature from 100° to 250° C. in the presence of a catalytic amount of hydroquinone in each case.

Compound (D″) is prepared by reacting the aldehyde (C″) with 0.5 to 5 mol equivalent of Wittig reagent such as carbomethoxyethylidene triphenylphosphorane or the like or an anion made from Wittig-Horner reagent such as ethyl 2-(diethylphosphono)propionate, ethyl 2-(dimethylphosphono)propionate or the like at temperature from —50° to 100° C. in a solvent such as diethyl ether, THF, DMF, dichloromethane or the like.

Compound (D″), when treated with 0.5 to 10 mol equivalent of metal hydride complex such as lithium aluminium hydride or the like at temperature from —70° to 100° C. in an ether solvent such as diethyl ether, THF or the like or with 0.5 to 10 mol equivalent of metal hydride such as dibutyialuminium hydride or the like at temperature from —70° to 100° C. in a hydrocarbon solvent such as benzene, toluene, n-hexane, n-heptane or the like, gives Compound (E″), which is a compound of formula I wherein n is 1, X is hydroxyl group and R is a group of formula:

$$-\overset{CHO}{\underset{|}{CH}}=CCH(CH_3)_2$$

which is the same as Compound (E′) in the synthetic route 2.

Compound (F) can be prepared from Compound (E″) by halogenating the allylic alcoholic without allyl rearrangement as previously described in the synthetic route 2. Compound (E″), when treated in the same manner as mentioned above, gives sarcophytol A.

As can be seen from the above, sarcophytol A can be prepared effectively from the compound (I) of the invention through various processes using or without using the intermediate F, which demonstrates that the compound (I) is highly useful and important for the attainment of the purpose of the invention.

Following Examples are provided for purposes of illustration only and are not to be construed as limiting the scope of the instant invention in any way.

PREPARATION 1

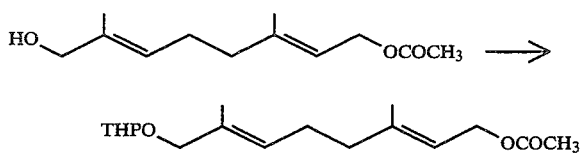

A mixture of 8-acetoxy-2,6-dimethyl-2,6-octadien-1-ol (1.81 g, 8.52 mmol) and dihydropyran (1.17 ml, 12.8 mmol) in dichloromethane (6 ml) was stirred, and p-toluenesulfonic acid (40 mg) was added thereto, and the mixture was stirred at room temperature for 30 minutes. After addition of saturated aqueous sodium bicarbonate (30 ml), the product was extracted with hexane/ether (5:1.2) (30 ml). The extract was dried over $Na_2SO_4$ and evaporated in vacuo to remove the solvent to give a residue, which was purified with silica gel column chromatography to give 1-acetoxy-8-(2-tetrahydropyranyl)oxy-3,7-dimethyl-2,6-octadiene (2.42 g, 96%).

PREPARATION 2

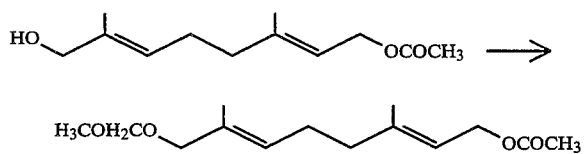

A mixture of 8-acetoxy-2,6-dimethyl-2,6-octadien-1-ol (110 mg, 0.52 mmol) and triethylamine (0.25 ml, 1.83 mmol) and chloromethyl methyl ether (0.069 ml, 0.92 mmol) in acetonitrile (2 ml) was refluxed with stirring for hours. After addition of water (3 ml) to the reaction mixture, the product was extracted several times with ether (5 ml). The extract was dried over $Na_2SO_4$ and evaporated in vacuo to remove the solvent to give a residue, which was then subjected to silica gel column chromatography to give he aimed 1-acetoxy-8-(2-methoxymethyl)oxy-3,7-dimethyl-2,6-octadiene (109 mg, 82%).

PREPARATION 3

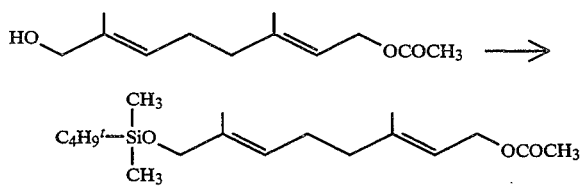

8-Acetoxy-2,6-dimethyl-2,6-octadien-1-ol in dimethylformamide (4 ml) was stirred on an ice bath. To the solution were added imidazole (338 mg, 4.96 mmol) and chlorodimethyl t-butylsilane (410 mg, 2.73 mmol), and the mixture was stirred at room temperature for one hour. After addition of water (30 ml) to the reaction mixture, the product was extracted with hexane (20 mlx2). The extract was dried over $MgSO_4$ and evaporated in vacuo to remove the solvent to give a residue, which was subjected to silica gel column chromatography to obtain 1-acetoxy-8-(dimethyl t-butylsilyl )oxy-3,7-dimethyl-2,6-octadiene (606 mg, 75% ) .

EXAMPLE 1

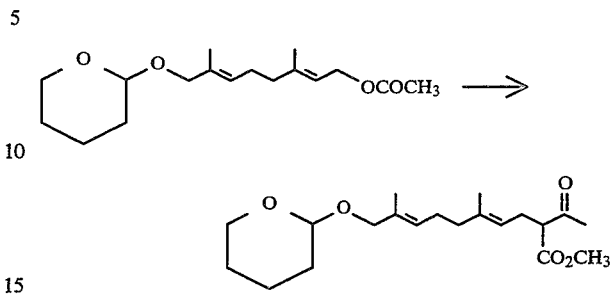

To a solution of 1-acetoxy-8-(2-tetrahydropyranyl)oxy-3,7-dimethyl-2,6-octadiene (1.08 g, 3.64 mmol ) in tetrahydrofuran (6 ml ) were added under nitrogen atmosphere triphenylphosphine (105 mg, 0.4 mmol) and tetrakis(triphenylphosphine)paradium (168 mg, 0.15 mmol), and the mixture was stirred at room temperature for 5 minutes. To the mixture were added a sodium salt of methyl acetoacetate in tetrahydrofuran (25 ml) which has been prepared from sodium hydride (305 mg, 12.7 mmol) and methyl acetoacetate (1.57 ml, 14.6 mmol), and the mixture was refluxed for 5 hours. After addition of water (10 ml) and ether (30 ml), the reaction mixture was stirred well, and the organic layer was separated. The aqueous layer was extracted with ether (5 ml), and the extract was dried over $Na_2SO_4$ and evaporated in vacuo to remove the solvent to give a residue, which was then subjected to silica gel column chromatography to obtain purified methyl 2-acetyl-5,9-dimethyl-10-(2-tetrahydropyranyl)oxy-4,8-decadienate (1.06 g, 83%).

IR(film)cm$^{-l}$; 2950, 2870, 1750, 1722, 1440, 1360, 1201, 1150, 1022.

NMR(CDCl$_3$, 250 MHz)δppm; 1.45–1.92(m, 6H, C(O)H$_2$—CH$_2$—CH$_2$—CH$_2$—CHO—), 1.63, 1.65(2s, 6H, 2x—CH$_3$C=CH—), 1.94–2.15(m, 4H, —C=CH—CH$_2$—CH$_2$—C=CH—), 2.22(s, 3H, CH$_3$C=O), 3.46(t, J=7.5 Hz, 1H, —CHCO2—), 3.53(m, 1H, —CH2—CHaHb—O—), 3.73(s, 3H, CO2CH$_3$), 3.83, 4.09(2d, J=11.8 Hz, 2H, —OCH$_2$C=CH—), 3.82–3.94(m, 1H, —CH$_2$—CHaHb—O—), 4.60(t, J=3.4 Hz, 1H, —O-CHO—), 5.04(t, J=7.3 Hz, 1H, —C=CH—CH$_2$—), 5.38(t, J=6.2 Hz, 1H, —C=CH—CH$_2$—).

EXAMPLE 2

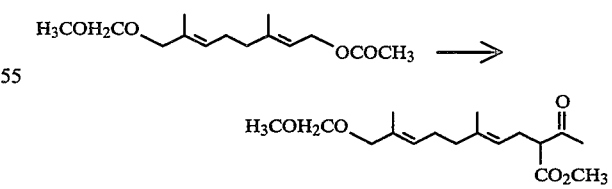

To a solution of 1-acetoxy-8-(methoxymethyl)oxy-3,7-dimethyl-2,6-octadiene (600 mg, 2.34 mmol) in tetrahydrofuran (6 ml) were added under nitrogen atmosphere triphenylphosphine (60 mg, 23 mmol) and tetrakis(triphenylphosphine)paradium (108 mg, 0.09 mmol), and the mixture was stirred at room temperature for 15 minutes. To the mixture were added a sodium salt of methyl acetoacetate in tetrahydrofuran (25 ml)

which has been prepared from sodium hydride (225 mg, 9.36 mmol) and methyl acetoacetate (1.26 ml, 11.7 mmol), and the mixture was refluxed for 2 hours. After addition of water (40 ml) and ether (50 ml), the reaction mixture was stirred well, and the organic layer was separated. The aqueous layer was extracted with ether (50 ml), and the extract was dried over $Na_2SO_4$ and evaporated in vacuo to remove the solvent to give a residue, which was then subjected to silica gel column chromatography to obtain purified methyl 2-acetyl-5,9-dimethyl-10-(methoxymethyl)oxy-4,8-decadienate (670 mg, 92%).

IR(film)cm$^{-1}$; 2930, 1745, 1720, 1438, 1355, 1208, 1150 1100, 1040, 920.

$^1$H NMR(CDCl$_3$, 250 MHz)δppm; 1.63, 1.65(2s, 6H, CH$_3$C=CH—x2), 1.93-2.17(m, 4H, —C=CH—CH$_2$—CH$_2$—C=CH—), 2.22(s, 3H, COCH$_3$), 2.56(t, J=7.4 Hz, 2H, —C=CH—CH2—CH(CO2CH$_3$)—), 3.38(s, 3H, CH$_3$OCH$_2$O—), 3.46(t, J=7.5 Hz, 1H, CH(CO2CH$_3$)), 3.73(s, 3H, CO2CH$_3$), 3.92(s, 2H, —OCH$_2$C=CH—), 4.61(s, 2H, —OCH$_2$O—), 5.04(t, J=7.3 Hz, 1H, —C=CH—CH2—), 5.38(t, J=6.7 Hz, 1H, —C=CH—CH2—).

EXAMPLE 3

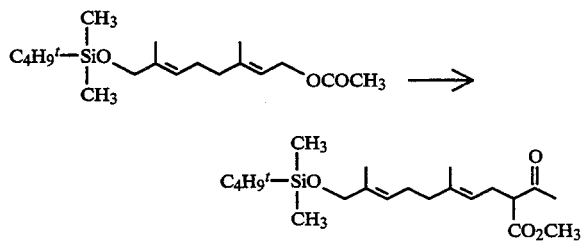

To a solution of 1-acetoxy-8-(dimethoxy t-butylsilyl)oxy-3,7-dimethyl-2,6-octadiene (600 mg, 1.84 mmol) in tetrahydrofuran (5 ml) were added under nitrogen atmosphere triphenylphosphine (47 mg, 0.18 mmol) and tetrakis(triphenylphosphine)paradium (81 mg, 0.07 mmol), and the mixture was stirred at room temperature for 15 minutes. To the mixture was added a sodium salt of methyl acetoacetate in tetrahydrofuran (20 ml) which has been prepared from sodium hydride (92 mg, 8.0 mmol) and methyl acetoacetate (0.99 ml, 9.20 mmol), and the mixture was refluxed overnight. After addition of water (10 ml) and ether (30 ml), the reaction mixture was stirred well, and the organic layer was separated. The aqueous layer was extracted with ether (5 ml×2), and the extract was dried over $Na_2SO_4$ and evaporated in vacuo to remove the solvent to give a residue, which was then subjected to silica gel column chromatography to obtain purified methyl 2-acetyl-10-(dimethyl t-butylsilyl)oxy-5,9-dimethyl-4,8-decadienate (620 mg, 88%). IR(film)cm$^{-1}$; 2970, 2940, 2910, 2860, 1745, 1722, 1435, 1360, 1250, 1065, 837, 775.

$^1$H NMR(CDCl$_3$, 250 MHz)δppm; 0.06, (s, 6H, (CH$_3$)$_2$Si), 0.90(s, 9H, (CH$_3$)$_3$CSi), 1.59, 1.63(2s, 6H, 2xCH$_3$C=CH—) , 1.92-2.15(m, 4 H, —C=CH—CH$_2$—CH$_2$—C=CH—), 2.22 (s, 3H, —CHCH$_3$), 2.55(t, J=7.4 Hz, 2H, —C=CH—CH2—CH(CO2CH$_3$)), 3.46(t, J=7.4 Hz, 1H, —CH(CO2CH$_3$)), 3.73(s, 3H, —CO2CH$_3$), 3.99(s, 2H, SiOCH$_2$), 5.04(t, J=6.7 Hz, 1H, —C=CH—CH2—), 5.33(t, J=6.8 Hz, 1H, —C=CH—CH2—).

EXAMPLE 4

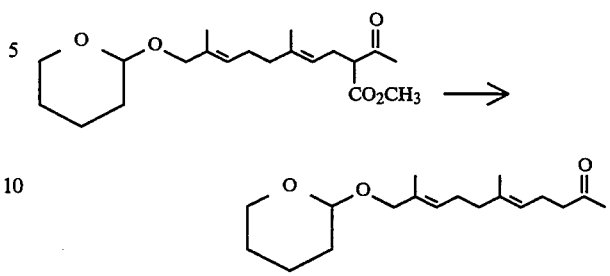

To a solution of methyl 2-acetyl-5,9-dimethyl-10-(2-tetrahydropyranyl)oxy-4,8-decadienate (370 mg, 1.05 mmol) in methylsulfoxide (2 ml) were added sodium chloride (180 mg, 3.08 mmol) and water (0.1 ml), and the mixture was stirred at 150° C. After four hours, the reaction mixture was allowed to cool to room temperature, and water (15 ml) was added thereto. The product was extracted with ether (20 ml×2). The extract was dried over $Na_2SO_4$, and concentrated to give a residue, which was then purified with silica gel column chromatography to obtain 6,10-dimethyl-11-(2-tetrahydropyranyl)oxy-5,9-undecadien-2-one (70%). IR(film)cm$^{-1}$; 2950, 2880, 1720, 1442, 1358, 1120, 1078, 1024, 905, 870, 815.

$^1$H NHR(CDCl$_3$, 250 MHz)δppm; 1.45-1.90(m, 6H, —OCH$_2$—CH$_2$—CH$_2$—CH$_2$—CH(O)), 1.62, 1.65(2s, 6H, (CH$_3$)C=CH—CH$_2$—CH$_2$—(CH$_3$)C=CH—), 1.96-2.20(m, 4H, —C=CH—CH$_2$—CH$_2$—C=CH—), 2.14(s, 3H, COCH$_3$), 2.26(q, J=7.1 Hz, 2H, —C=CH—CH$_2$—CH$_2$CO—), 2.46(t, J=7.1 Hz, 2H, —CH$_2$COCH$_3$), 3.45-3.55(m, 1H, OCHaHb—CH$_2$—CH$_2$—CH$_2$—CH(O)), 3.84, 4.10(2d, J=11.5 Hz, —OCH$_2$C=CH—), 3.80-3.95(m, 1H, OCHaHb—CH$_2$—CH$_2$—CH$_2$—), 4.60(t, J=3.6 Hz, 1H, CH(O)), 5.08(t, J=7.1 Hz, —C=CH—CH$_2$—CH$_2$—C=CH—), 6.9(t, J=6.9 Hz, 1H, —C=CH—CH$_2$—CH$_2$—C=CH—).

EXAMPLE 5

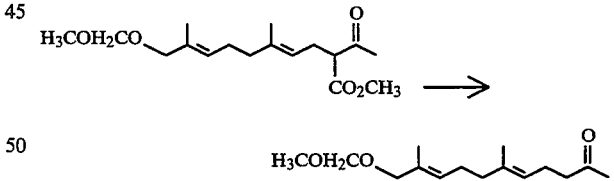

To a solution of methyl 2-acetyl-5,9-dimethyl-10-(methoxymethyl)oxy-4,8-decadienate (420 mg, 1.37 mmol) in methylsulfoxide (4 ml) were added sodium chloride (160 mg, 2.74 mmol) and water (0.1 ml), and the mixture was stirred at 150° C. After five hours, the reaction mixture was allowed to cool to room temperature, and water (10 ml) was added thereto. The product was extracted with ether (20 ml×2). The extract was dried over $Na_2SO_4$, and concentrated to give a residue, which was then purified with silica gel column chromatography to obtain 6,10-dimethyl-11-(methoxymethyl)oxy-5,9-undecadien-2-one (358 mg, 67%).

IR(film)cm$^{-1}$; 2940, 1720, 1440, 1358, 1150, 1100, 1050, 920.

$^1$H NMR(CDCl$_3$, 250 MHz)δppm; 1.62, 1.66(2s, 6H, 2xCH$_3$C=CH—), 1.94-2.32(m, 6H, —C=CH—CH 2—CH$_2$—C=CH—CH$_2$—), 2.14(s, 3H, COCH$_3$), 2.46(t, J=7.3 Hz, 2H, —CH$_2$COCH$_3$), 3.38(s, 3H, CH$_3$O), 3.92(s, 2H, OCH$_2$C=CH—), 4.61(s, 2H, —OCH$_2$C—), 5.08(t, J=6.1 Hz, 1H, —C=CH—CH$_2$—), 5.40(t, J=6.7 Hz, 1H, —C=CHCH$_2$—).

EXAMPLE 6

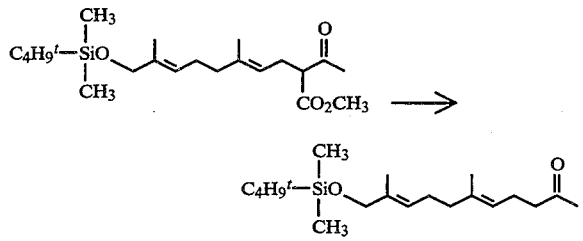

To a solution of methyl 2-acetyl-10-(dimethyl t-butylsilyl)oxy-5,9-dimethyl-4,8-decadienate (96 mg, 0.25 mmol) in hexamethylphosphoric triamide (0.5 ml) were added sodium iodide (45 mg, 0.30 mmol) and water (0.01 ml), and the mixture was stirred at 150° C. After two hours, the reaction mixture was allowed to cool to room temperature, and water (2 ml) was added thereto. The product was extracted with ether (5 mlx2). The extract was dried over Na$_2$SO$_4$, and concentrated to give a residue, which was then purified with silica gel column chromatography to obtain 6,10-dimethyl-11-(dimethyl t-butylsilyl)oxy-5,9-undecadien-2-one (57 mg, 70%).

IR(film)cm$^{-1}$; 2970, 2950, 2910, 2870, 1725, 1465, 1360, 1255, 1155, 1110, 1070, 837, 775, 662.

$^1$H NMR(CDCl$_3$, 250 MHz)δppm; 0.06(s, 6H, (CH$_3$)$_2$Si), 0.91(s, 9H, (CH$_3$)$_3$CSi), 1.59, 1.62(28, 6H, 2x—C=CH—CH$_2$—), 1.92-2.32(m, 6H, —CH=CH—CH$_2$—CH$_2$—C=CH—CH$_2$—), 2.14(s, 3H, COCH$_3$), 2.46(t, J=8.7 Hz, 2H, CH$_2$COCH$_3$), 4.00(s, 2H, SiOCH$_2$—), 5.08, 5.35(2m, 2H, —C=CH—CH$_2$—x2).

EXAMPLE 7

The procedures described in Examples 4-6 were repeated except that methyl 2-acetyl-5,9-dimethyl-10-(benzoyl)oxy-4,8-decadienate was employed as a starting material to give 6,10-dimethyl-11-(benzoyl)oxy-5,9-undecadien-2-one.

EXAMPLE 8

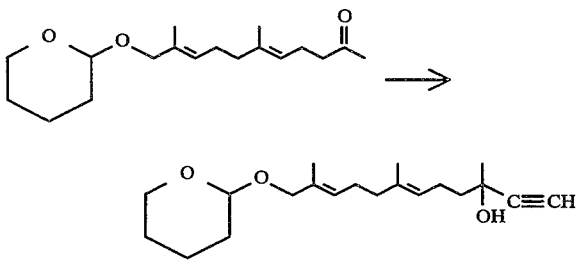

A solution of 6,10-dimethyl-11-(2-tetrahydropyranyl)oxy-5,9-undecadien-2-one (90 mg, 0.31 mmol) in tetrahydrofuran (5 ml) was stirred on an ice bath under argon atmosphere. To the solution was added lithium acetylide ethylenediamine complex (180 mg, 1.95 mmol), and the mixture was warmed to room temperature and stirred for 3 hours. After addition of saturated aqueous ammonium chloride (2 ml), the reaction mixture was extracted with ether. The extract was dried over Na$_2$SO$_4$ and evaporated in vacuo to remove the solvent to give a crude product, which was purified with silica gel column chromatography to obtain 3,7,11-trimethyl-12-(2-tetrahydropyranyl)oxy-6,10-dodecadien-1-in-3-ol (75 mg, 75%).

IR(film)cm$^{-1}$; 3440, 3320, 2950, 2880, 2200, 1440, 1450, 1382, 1360, 1260, 1200, 1180, 1115, 1075, 1020, 905, 865, 810.

$^1$H NMR(CDCl$_3$, 250 MHz)δppm; 1.50(s, 3H, CH$_3$C(OH)), 1.45-1.90(m, 8H, OCH$_2$—CH$_2$—CH$_2$—CH$_2$—CH(O), —CH$_2$C(OH), 1.65(s, 6H, 2xCH$_3$C=CH—) , 2.00-2.40(m, 7H, —C=CH—CH$_2$—CH2—C=CH—CH$_2$—, OH), 2.46(s, 1H, —Cü—C—H), 3.45-3.57(m, 1H, —OCHaHb—CH$_2$—), 3.84, 4.10(2d, J=11.5 Hz, 2H, OCH$_2$C=CH—), 3.80-3.94(m, 1H, —OCHaHb—CH$_2$—), 4.60(t, J=3.4 Hz, 1H, —O-CHO—), 5.19(t, J=6.7 Hz, 1H, —C=CH—CH$_2$—), 5.41(t, J=6.7 Hz, 1H, —C=CH—CH$_2$—).

EXAMPLE 9

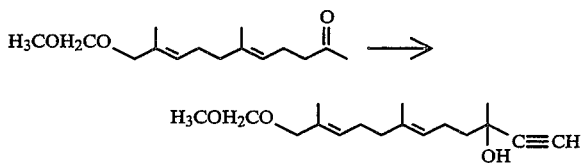

A solution of 6,10-dimethyl-11-(methoxymethyl)oxy-5,9-undecadien-2-one (67 mg, 0.26 mmol) in tetrahydrofuran (2 ml) was stirred on an ice bath under argon atmosphere. To the solution was added lithium acetylide ethylenediamine complex (30 mg, 0.33 mmol), and the mixture was warmed to room temperature and stirred for 3 hours. After addition of saturated aqueous ammonium chloride (2 ml), the reaction mixture was extracted with ether. The extract was dried over Na$_2$SO$_4$ and evaporated in vacuo to remove the solvent to give a crude product, which was purified with silica gel column chromatography to obtain 3,7,11-trimethyl-12-(methoxymethyl)oxy-6,10-dodecadien-1-in- 3-ol ( 61 mg, 83% ).

IR(film)cm$^{-1}$; 3450, 3300, 2940, 1445, 1370, 1148, 1045, 918.

$^1$H NMR(CDCl$_3$, 250 MHz)δppm; 1.05(s, 3H, CH$_3$C(O)), 1.55-1.84(m, 9H, 2xCH$_3$C=CH—, OH), 2.00-2.40(m, 6H, —C=CH—CH$_2$—CH$_2$—C=CH—CH$_2$—), 2.46(s, 1H, —C=C—H), 3.78(s, 3H, CH$_3$O), 3.92(s, 2H, —OCH$_2$C=CH—), 4.61(s, 2H, OCH$_2$O), 5.19(t, J=6.2 Hz, 1H, —C=CH—CH$_2$—), 5.41(t, J=6.2 Hz, —C=CH—CH$_2$—).

EXAMPLE 10

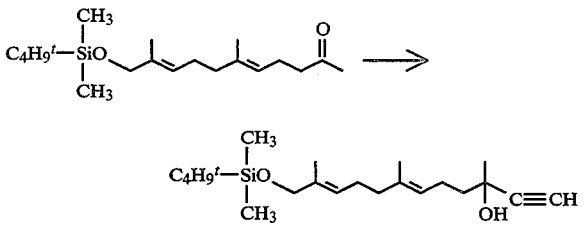

A solution of 6,10-dimethyl-11-(dimethyl t-butylsilyl)oxy-5,9-undecadien-1-one (71 mg, 0.22 mmol) in tetrahydrofuran (2 ml) was stirred on an ice bath under argon atmosphere. To the solution was added lithium acetylide ethylenediamine complex (90 mg, 0.98 mmol), and the mixture was warmed to room temperature and stirred for 4 hours. After addition of saturated aqueous ammonium chloride (2 ml), the reaction mixture was extracted with ether. The extract was dried over Na$_2$SO$_4$ and evaporated in vacuo to remove the solvent to give a crude product, which was purified with silica gel column chromatography to obtain 3,7,11-trimethyl-12-(dimethyl t-butylsilyl)oxy-6,10-dodecadien-1-in-3-ol (51 mg, 67%).

IR(film)cm$^{-1}$; 3450, 3320, 2960, 2940, 2910, 2860, 1460, 1360, 1250, 1110, 1065, 835, 775.

$^1$H NMR(CDCl$_3$, 250 MHz)δppm; 0.06(s, 6H, (CH$_3$)$_2$Si), 0.91(s, 9H, (CH$_3$)$_3$Si), 1.50(s, 3H, —CH$_2$—C(OH)(CH$_3$)—C≡H), 1.59, 1.66(2s, 6H, 2xCH$_3$C=CH—), 1.68-1.76(m, 2H, 13 CH$_2$C(OH)—), 1.94-2.36 (m, 7H, —C=CH—CH$_2$—CH$_2$—C=CH—CH$_2$—, OH ), 2.46 ( s, 1H, —C≡CH), 4.00(s, 2H, OCH$_2$—C=CH—), 5.19(t, J=7.1 Hz, 1H, —C=CH—CH$_2$—), 5.36(t, J=6.9 Hz, 1H, —C=CH—CH$_2$—).

EXAMPLE 11 and 12

The procedure described in Example 9 was repeated except that 6,10-dimethyl-11-acetoxy-5,9-undecadien-2-on or 6,10-dimethyl-11-(benzoyl)oxy-5,9-undecadien-2-one was employed as a starting material to give 3,7,11-trimethyl-12-acetoxy-6,10-dodecadien-1-in-3-ol and 3,7,11-trimethyl-12-(benzoyl)oxy-6,10-dodecadien-1-in-3-ol.

EXAMPLE 13

The procedures described in Examples 8 and 10 were repeated except that 2,6-dimethyl-2,6-dodecadien-10-on-1-ol was employed as a starting material to give 2,6,10-trimethyl-2,6-dodecadien-11-in-1,10-diol.

EXAMPLE 14

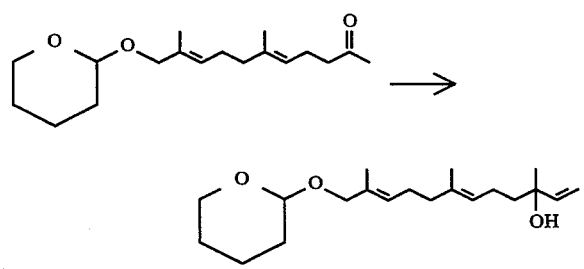

A solution of 6,10-dimethyl-11-(2-tetrahydropyranyl)oxy-5,9-undecadien-2-one (80 mg, 0.27 mmol) in tetrahydrofuran (3 ml) was stirred on an ice bath under argon atmosphere. To the solution was added vinylmagnesium bromide in tetrahydrofuran (0.3 ml, 0.3 mmol, 1.0M), and the mixture was warmed to room temperature and stirred for 10 hours. After addition of saturated aqueous ammonium chloride (2 ml), the reaction mixture was extracted with ether. The extract was dried over Na$_2$SO$_4$ and evaporated in vacuo to remove the solvent to give a crude product, which was purified with silica gel column chromatography to obtain 3,7,11-trimethyl-12-(2-tetrahydropyranyl)oxy-1,6,10-dodecatrien-3-ol (61 mg, 70%).

IR(film)cm$^{-1}$; 3460, 2950, 2880, 1200, 1118, 1075, 1022, 905, 865, 810.

$^1$H NMR(CDCl$_3$, 250 MHz)δppm; 1.28(s, 3H, C(OH)CH$_3$), 1.65-1.92(m, 8H, —OCH$_2$—CH$_2$—CH$_2$—CH(O)—), CH$_2$—C(OH)), 1.95-2.40(m, 7H, C=CH—CH$_2$—CH$_2$—C=CH—CH$_2$—, OH), 3.45-3.55(m, 1H, —OCHaHb—CH$_2$—), 3.84, 4.10(2d, J=11.6 Hz, 2H, —OCH$_2$C=CH$_2$—), 3.80-3.95(m, 1H, —OCHaHb—CH$_2$—), 4.60(t, J=3.4 Hz, 1H, OCH(O)), 5.06(dd, J=1.3, 10.7 Hz, 1H, —CH=CHaHb), 5.14(m, 1H, —C=CH—CH$_2$—), 5.22(dd, J=1.3, 17.4 Hz, 1H, —CH=CHaHb), 5.41(t, J=6.3 Hz, 1H, —C=CH—CH$_2$—), 5.92(dd, J=10.7, 17.4 Hz, 1H, —CH=CH$_2$).

EXAMPLE 15

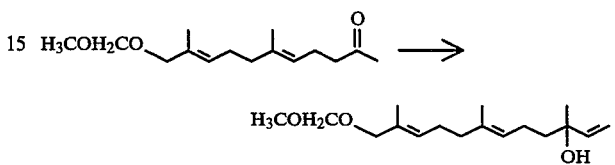

A solution of 6,10-dimethyl-11-(methoxymethyl)oxy-5,9-undecadien-2-one (60 mg, 0.24 mmol) in tetrahydrofuran (2 ml) was stirred on an ice bath under argon atmosphere. To the solution was added vinylmagnesium bromide in tetrahydrofuran (1.0 ml, 1.0 mmol, 1.0M), and the mixture was warmed to room temperature and stirred for 4 hours. After addition of saturated aqueous ammonium chloride (2 ml), the reaction mixture was extracted with ether. The extract was dried over Na$_2$SO$_4$ and evaporated in vacuo to remove the solvent to give a crude product, which was purified with silica gel column chromatography to obtain 3,7,11-trimethyl-12-(methoxymethyl)oxy-1,6,10-dodecatrien-3-ol (54 mg, 80%).

IR(film)cm$^{-1}$; 3480, 2940, 1450, 1370, 1210, 1150, 1100, 1045, 920, 845, 685.

$^1$H NMR(CDCl$_3$, 250 MHz)δppm; 1.28(s, 3H, CH$_3$C(OH)), 1.60, 1.66(2s, 6H, 2xCH$_3$—CH=C—), 1.52-1.72(m, 2H, —CH$_2$—C(OH)), 1.95-2.20(m, 7H, —C=CH—CH$_2$—CH$_2$—C=CH—CH$_2$—, OH), 3.38(s, 3H, CH3O), 3 92(s, 2H, —OCH$_2$C=CH—), 4.61(s, 2H, —OCH$_2$O), 5.06(dd, J=1.3, 10.7 Hz, 1H, —CH=CHaHb), 5.14(t, J=7.2 Hz, 1H, —C=CH—CH$_2$—), 5.20(dd, J=1.3, 17.4 Hz, 1H, —CH=CHaHb), 5.41(t, J=6.9 Hz, 1H, —C=CH—CH$_2$—), 5.92(dd, J=10.7, 17.4 Hz, 1H, —CH=CH$_2$—) .

EXAMPLE 15

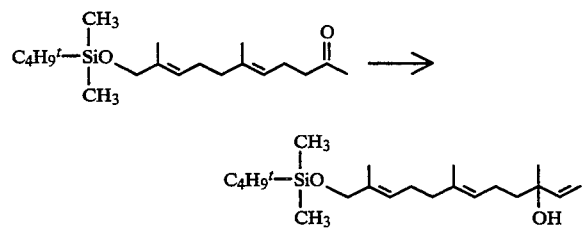

A solution of 6,10-dimethyl-11-(dimethyl-t-butylsilyl)oxy-5,9-undecadien-2-one (48 mg, 0.15 mmol) in tetrahydrofuran (2 ml) was stirred on an ice bath under argon atmosphere. To the solution was added vinylmagnesium bromide in tetrahydrofuran (10 ml, 1.0 mmol, 1.0M), and the mixture was warmed to room temperature and stirred for 4 hours. After addition of saturated aqueous ammonium chloride (2 ml), the reaction mixture was extracted with ether. The extract was dried over Na₂SO₄ and evaporated in vacuo to remove the solvent to give a crude product, which was purified with silica gel column chromatography to obtain 3,7,11-trimethyl-12-(dimethyl-t-butylsilyl)oxy-l,6,10-dodecatren-1-3-ol (32 mg, 60%).

IR(film)cm⁻¹; 3420, 2970, 2940, 2860, 1462, 1360, 1250, 150, 1070, 920, 835, 775, 662.

¹H NMR(CDCl₃, 250 MHz)δppm; 0.06(s, 6H, (CH₃)₂Si), 0.91(s, 9H, (CH₃)₃CSi), 1.28(s, 3H, —C(OH)(CH₃)—CH=CH₂), 1.60(s, 6H, 2xCH₃C=CH—), 1.46-1.73(m, 3H, —CH₂C(OH)(CH₃))—, 4.00(s, 2H, SiOCH₂—), 5.06(dd, J=1.3, 10.7 Hz, 1H, —CH=CHaHb), 5.14(m, 1H, —C=CH—CH₂—), 5.22(dd, J=1.3, 17.4 Hz, 1H, —CH=CHaHb), 5.36(m, 1H, —C=CH—CH₂—), 5.92(dd, J=10.7, 17.4 Hz, 1H, —CHCH₂—).

EXAMPLE 17

The procedure described in Example 14 was repeated except that 6,10-dimethyl-11-(benzoyl)oxy-5,9-undecadien-2-one was employed as a starting material to give 3,7,11-trimethyl-12-(benzoyl)oxy-l,6,10-dodecatrien-3-ol.

EXAMPLE 18

The procedures described in Examples 15 and 16 were repeated except that 2,6-dimethyl-2,6-undecadien-10-on-1-ol was employed as a starting material to give 2,6,10-trimethyl-2,6,11-dodecatrien-1,10-diol.

EXAMPLE 19

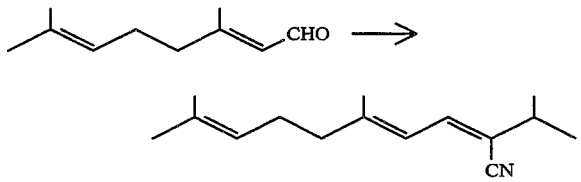

To a solution of 2-(diethylphosphono)isovaleronitrile (6.54 g, 30 mmol) in toluene (55 ml) was added a 0.5M solution of potassium bis(trimethylsilyl)amide in toluene (56 ml) with stirring on a cooling bath at −70° C. After 30 minutes, geranial (3.80 g, 25 mmol) was added thereto with continuous stirring at the same temperature, and then the reaction mixture was warmed up to room temperature. After addition of water to the mixture, the organic layer was extracted. The organic extract was washed with saturated aqueous sodium bicarbonate and saturated aqueous sodium chloride, dried over MgSO₄, and filtered. The filtrate was concentrated to give a residue, which was then subjected to silica gel column chromatography (solvent: n-hexane/ethyl acetate=100:1) to give 2-(1-methylethyl)-5,9-dimethyl-2,4,8-decatrienenitrile (4.87 g, 90%, 2Z:2E=22.4:1).

Spectral Data of 2Z Compound

IR(film)cm⁻¹; 2980, 2940, 2890, 2220, 1640, 1450, 1390, 1375, 1295, 1225, 1105, 1030.

¹H NMR(CDCl₃, 250 MHz)δppm; 1.17(d, J=6.8 Hz, 6H, CH(CH₃)₂), 1.61, 1.69(each bs, each 3H, —C=CCH₃), 1.83(d, J=1.2 Hz, 3H, —C=CCH₃), 2.-12.2(m, 4H, —CH₂CH₂—), 2.53(hep, J=6.8 Hz, 1H, CH(CH₃)₂), 5.08(m, 1H, —C=CH₂—), 6.28, 6.82(each d, J=11.5 Hz, each 1H, =CHC—CH=).

EXAMPLE 20

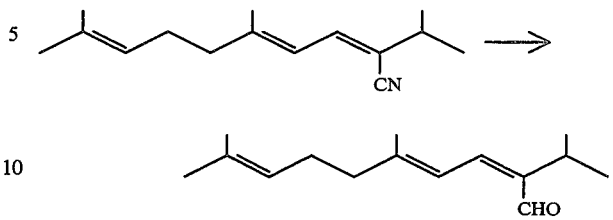

To a solution of 2-(1-methylethyl)-5,9-dimethyl-2,4,8-decatrienenitril (2Z compound, 217 mg, 1 mmol) in n-hexane (4 ml) was added a 1 M solution of diisobutylaluminium hydride in toluene (2 ml) with stirring under argon atmosphere at −70° C. After two-hour-stirring at the same temperature, water (0.8 ml) was added to the mixture followed by removal of the cooling bath and vigorous stirring. The resultant while precipitates were filtered and washed with n-hexane. The filtrate was combined with a 10% aqueous solution of oxalic acid and stirred for 3 hours. The organic layer was extracted and separated, washed with water, dried over MgSO₄, and concentrated. The above manipulation was conducted under argon atmosphere. The resultant residue was subjected to silica gel column chromatography (solvent: n-hexane/ethyl acetate=50:1) to obtain the aimed 2-(1-methylethyl)-5,9-dimethyl-2,4,8-decatrienal (198 mg, 90%).

IR(film)cm⁻¹; 2980, 2940, 2880, 1670, 1630, 1455, 1375, 1295, 1235, 1135, 1105, 1075.

NMR (CDCl₃, 250 MHz)δppm; 1.07(d, J=6.8 Hz, 6H, —CH(CH₃)₂), 1.62, 1.69(each bs, each 3H, —C=CCH₃), 1.89(d, J=1.0 Hz, 3H, —C=CCH₃), 2.-12.3(m, 4H, —CHhd 2CH₂—), 2.91(hep, J=6.8 Hz, 1H, —CH(CH₃)₂), 5.10(m, 1H, =CHCH₂—), 6.83 -7.1-4(each d, J=12.0 Hz, each 1H, =CH—CH=), 10.29(s, 1H, —CHO).

EXAMPLE 21

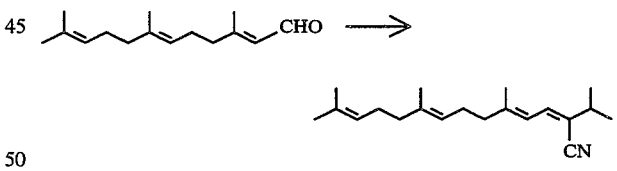

To a solution of 2-(diethylphosphono)isovaleronitrile (8.72 g, 40 mmol) in toluene (75 ml) was gradually added a 0.5M solution of potassium bis(trimethylsilyl)amide in toluene (75 ml) with stirring at −70° C. under argon atmosphere. The cooling bath was removed, and the reaction mixture was stirred at room temperature for 30 minutes. The reaction mixture was cooled to −70° C. again, and farnesol (5.88 g, 26.7 mmol) was added thereto with stirring, and the mixture was allowed to warm to room temperature. After addition of water, the organic layer was separated, washed with saturated aqueous sodium bicarbonate and then saturated aqueous sodium chloride, and dried over MgSO₄. The organic layer was separated from MgSO₄ by filtration and concentrated to give a residue, which was purified with silica gel column chromatography (solvent: n-hexane/ethyl acetate=100:1) to obtain the aimed 2 -(1-methylethyl)-5,9,13-trimethyl-2,4,8,12-tetradecatetraenenitrile (7.23 g, 96%; 2Z:2E=25.6:1).

Spectral Data of 2Z Compound

IR(film)cm⁻¹; 2980, 2940, 2210, 1640, 1450, 1390, 1290, 1225, 1110, 1030.

NMR(CDCl₃, 250 MHz)δppm; 1.14(d, J=6.8 Hz, 6H, CH(CH₃)₂), 1.58(bs, 3Hx2, —C=CCH₃), 1.65(bs, 3H, —C=CCH₃), 1.81(d, J=1.2 Hz, 3H, —C=CCH₃), 1.9-2.2(m, 8H, —CH₂CH₂—x2), 2.50(hep, J=6.8 Hz, 1H, —CH(CH₃)₂), 5.06(m, 1H, =CHCH₂—), 6.26, 6.80 each d, J=11.5 Hz, each 1H, =CH—CH=).

EXAMPLE 22

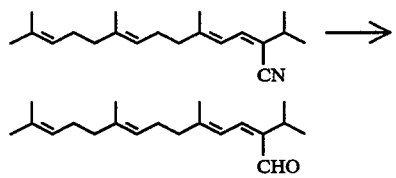

To a solution of 2-(1-methylethyl)-5,9,13-trimethyl-2,4,8,12-tetradecatetraenenitrile (856 mg, 3.0 mmol) in n-hexane (30 ml) was added a 0.5M solution of diisobutylaluminium hydride in toluene (6 ml) with stirring at −70° C. under argon atmosphere. After one hour, water (3 ml) was added, the cooling bath was removed, and the reaction mixture was stirred well. Resultant white precipitates were filtered and washed. The filtrate was concentrated to give a residue, which was dissolved in n-hexane (10 ml). The n-hexane solution was combined with a 0% aqueous solution of oxalic acid (5 ml) and stirred for 3 hours. The organic layer was extracted and separated, washed with water, dried over MgSO₄, and concentrated. The resultant residue was subjected to silica gel column chromatography (solvent: n-hexane/ethyl acetate=10:1) to obtain 2 -(1-methylethyl)-5,9,13-trimethyl-2,4,8,12-tetradecatetraenal (865 mg, 84%).

IR(film)cm⁻¹; 2980, 2940, 2210, 1640, 1450, 1390, 1290, 1225, 1110, 1030.

NMR(CDCl₃, 250 MHz)δppm; 1.07(d, J=6.8 Hz, 6H, —CH(CH₃)₂), 1.59, 1.61, 1.67(each bs, 3Hx3, —C=CCH₃), 1;89(d, J=1.0 Hz, 3H, —C=CCH₃), 2.0-2.2(m, 8H, —CH₂CH₂—x2), 2.91(hep, J=6.8 Hz, 1H, —CH(CH₃)₂), 5.10(m, 1H, —C=CCH₃), 6.81, 7.16(each d, J=12.0 Hz, each 1H, =CH—CH=), 10.29(s, 1H, —CHO).

EXAMPLE 23

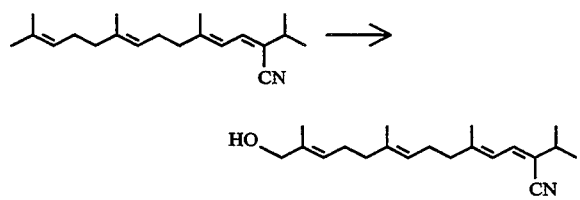

To a suspension of selenium dioxide (58 mg) and 2-hydroxybenzoic acid (365 mg) in methylene chloride (10.5 ml) was gradually added an aqueous solution of 80% t-butyl hydroperoxide (11.6 ml) with stirring on a water bath. After 30 minutes, 2-(1-methylethyl)-5,9,13-trimethyl-2,4,8,12-tetradecatetraenenitrile (7.56 g, 26.8 mmol) was added to the mixture, which was then allowed to stand at room temperature for 30 hours. Most of the solvent was removed by evaporation in vacuo, and the residue was dissolved in ether. The organic layer was washed with saturated aqueous sodium bicarbonate, dried over MgSO₄, and concentrated. The resultant residue was subjected to silica gel column chromatography to give the aimed 14-hydroxy-2-(1-methylethyl)-5,9,13-trimethyl-2,4,8,12-tetradecatetraenenitrile (2.53 g, 31%). The starting material was also recovered (3.10 g, 40%) in the column chromatography. The yield of the aimed product based on the consumed starting material was 52%.

IR(film)cm⁻¹; 3450, 2975, 2930, 2880, 2210, 1635, 1445, 1385, 1220, 1020.

NMR(CDCl₃, 250 MHz)δppm; 1.17(d, J=6.7 Hz, 6H, CH(CH₃)₂), 1.62, 1.67(each bs, each 3H, —C=CCH₃), 1.84(d, J=1.2 Hz, 3H, —C=CCH₃), 2.0-2.2(m, 8H, —CH₂CH₂—x2), 2.53(hep, J=6.7 Hz, 1H, —CH(CH₃)₂), 3.99(bs, 2H, —CH₂OH), 5.11(m, 1H, —CHCH₂—), 5.39(bt, J=5.5 Hz, 1H, —CHCH₂—), 6.28, 6.83(each d, J=11.5 Hz, each 1H, =CH—CH=).

EXAMPLE 24

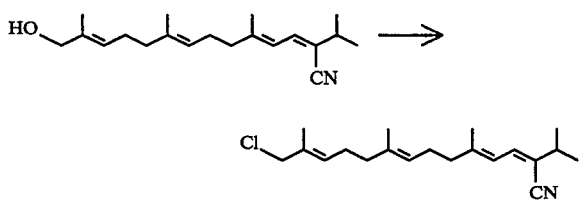

To a solution of 14-hydroxy-2-(1-methylethyl)-5,9,13-trimethyl-2,4,8,12-tetradecatetraenenitrile (904 mg, 3.0 mmol) in carbon tetrachloride (2 ml) was added triphenylphosphine (1.02 g, 3.9 mmol), and the mixture was heated under reflux for one hour. Most of carbon tetrachloride was removed by evaporation in vacuo, and n-hexane was added to the residue. The resultant mixture was filtered and washed and the filtrate was concentrated to give a residue, which was then subjected to silica gel column chromatography (solvent: n-hexane/ethyl acetate=10:1) to obtain the aimed 14-chloro compound (890 mg, 93%).

IR(film)cm⁻¹; 2980, 2940, 2880, 2215, 1635, 1445, 1390, 1265, 1025.

NMR(CDCl₃, 250 MHz)δppm; 1.14(d, J=6.8 Hz, 6H, CH(CH₃)₂), 1.59, 1.64(each bs, each 3H, —C=CCH₃), 1.81(d, J=1.0 Hz, 3H, —C=CCH₃), 1.9-2.2(m, 8H, —CH₂CH₂—x2), 2.50(hep, J=6.8 Hz, 1H, —CH(CH₃)₂), 3.96(bs, 2H, —CH₂OH), 5.08(m, 1H, —CHCH₂—), 5.36(bt, J=5.5 Hz, 1H, =CHCH₂—), 6.25, 6.80(each d, J=11.5 Hz, each 1H, =CH—CH=).

The following Reference Examples illustrate a method of preparation of sarcophytol A by the use of the compounds obtained in the foregoing Examples.

REFERENCE EXAMPLE 1

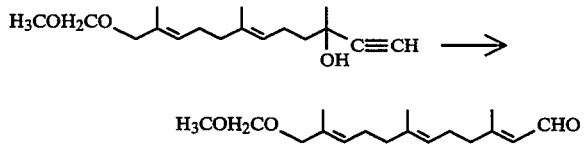

A solution of 3,7,11-trimethyl-12-(methoxymethyl)oxy-6,10-dodecadien-1-in-3-ol (175 mg, 0.62 mmol), tris(triphenylsilyl)vanadate (49 mg, 0.062 mmol), and benzoic acid (7.6 mg, 0.062 mmol) in xylene (2 ml) was stirred on an oil bath at 140° C. After two-hour-stirring, the solution was allowed to cool to room temperature and concentrated. The resultant residue was subjected to silica gel column chromatography to obtain 12-(methoxymethyl)oxy-3,7,11-trimethyl-2,6,10-dodecatrienal (88 mg, 50%).

IR(film)cm$^{-1}$; 2950, 1675, 1450, 1385, 1198, 1157, 1120, 1105, 1050, 925, 850.

$^1$H NMR(CDCl$_3$, 250 MHz)δppm; 1.57, 1.62, 2.13(each s, each 3H, CH$_3$C=CH—), 1.93–2.30(m, 8H, 2x—C=CH—CH$_2$—CH$_2$—), 3.33(s, 3H, CH$_3$O), 3.88(s, 2H, —OCH$_2$C=CH—), 4.57.(s, 2H, —OCH$_2$O—), 5.06, 5.36(each m, each 1H, —C=CH—CH$_2$—), 5.84(d, J=8.2 Hz, 1H, —C=CH—CHO), 9.96 (d, J=8.2 Hz, 1H, —C=CH—CHO).

REFERENCE EXAMPLE 2

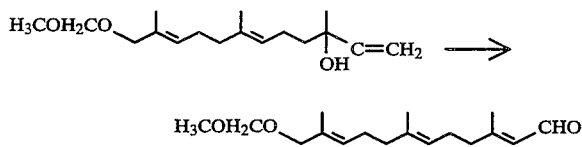

A solution of 3,7,11-trimethyl-12-(methoxymethyl)oxy-1,6,10-dodecatrien-3-ol (460 mg, 1.6 mmol) in dichloromethane (30 ml) was added pyridinium chlorochromate (690 mg, 3.2 mmol), and the mixture was stirred at room temperature for 8 hours. After addition of a mixture of hexane, ethyl acetate, and ether (3:1:1) (100 ml), the mixture was stirred and insoluble materials were filtered. The filtrate was concentrated in vacuo, and the residue was purified with silica gel column chromatography to give 12-(methoxymethyl)oxy-3,7,11-trimethyl-2,6,10-dodecatrienal (233 mg, 52%). The physico-chemical properties of the product was the same as those described in Reference Example 1.

REFERENCE EXAMPLE 3

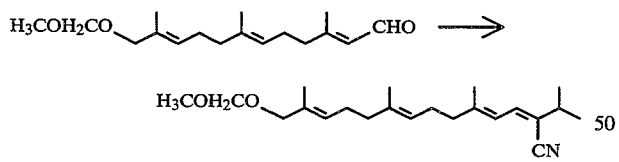

To a solution of 2-(diethylphosphono)isovaleronitrile (316 mg, 1.44 mmol) in toluene (1 ml) was dropwise added a 1.0M solution of lithium bis(trimethylsilyl)amide in hexane (1.3 ml, 1.3 mmol) with stirring at −70° C. After 30 minutes, 12-(methoxymethyl)oxy-3,7,11-trimethyl-2,6,10-dodecatrienal (130 mg, 0.46 mmol) in toluene (2 ml) was added at the same temperature, and the mixture was allowed to warm to room temperature over about 3 hours. An aqueous ammonium chloride (6 ml) was added and the mixture was extracted with hexane. The extract was dried over Na$_2$SO$_4$ and evaporated in vacuo to remove the solvent to give a residue, which was then subjected to silica gel column chromatography (solvent: n-hexane/ethyl acetate=20:1) to obtain the aimed 2-(1-methylethyl)-14-(methoxymethyl)oxy-5,9,13-trimethyl-2,4,8,12-tetraenenitrile (135 mg, 85%).

IR(film)cm$^{-1}$; 2980, 2945, 2900, 2310, 1640, 1150, 1050. 1N NMR(CDCl$_3$, 250 MHz)δppm; 1.17(d, J=6.8 Hz, 6H, (CH$_3$)$_2$CH—), 1.61, 1.67, 1.84(each s, each 3H, CH$_3$C=CH—), 1.96–2.21(m, 8H, —C=CH—CH$_2$—CH$_2$—C=CH—CH$_2$—CH$_2$—), 2.53 (hep, J=6.8 Hz, 1H, —CH(CH$_3$)$_2$), 3.38(s, 3H, CH$_3$O—), 3.92(s, 2H, —OCH$_2$O—), 4.62 (s, 2H, —O—CH$_2$—C=CH—), 5.10 (brs, 1H, —C=CH—), 5.42(brt, J=6.4 Hz, 1H, —C=CH—), 6.28, 6.82(each d, J=11.5 Hz, each 1H, —C=CH—CH=C(CN)—).

REFERENCE EXAMPLE 4

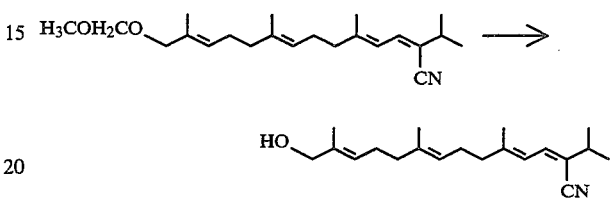

To the product obtained in Reference Example 3 (135 mg, 0.39 mmol) in methanol (5 ml) was added a trace amount of conc. HCl, and the mixture was heated with stirring at 60° C. for 6 hours. After addition of saturated aqueous sodium bicarbonate (20 ml), the reaction mixture was extracted with ether (20 mlx2). The extract was dried over MgSO$_4$ and evaporated in vacuo to remove the solvent. The resultant residue was purified with silica gel column chromatography (solvent: n-hexane/ether=5:1) to obtain the 14-hydroxy compound (96 mg, 82%).

IR(film)cm$^{-1}$; 3460, 2980, 2930, 2210, 1635, 1450, 1020.

$^1$H NMR(CDCl$_3$, 250 MHz)δppm; 1.14(d, J=6.8 Hz, 6H, (CH$_3$)$_2$CH—), 1.58 (m, 4H, CH$_3$C=CH—, —OH), 1.65(s, 3H, CH$_3$C=CH—), 1.81(d, J=1.1 Hz, 3H, CH$_3$C=CH—), 1.92–2.25(m, 8H, —C=CH—CH$_2$—(CH$_3$)C=CH—CH$_2$—CH$_2$—), 2.51 (hep, J=6.8 H (CH$_3$)$_2$CH—), 3.97(d, J=5.9 Hz, 2H, CH$_2$OH), 5.08(brs, 1H, —C=CH—), 5.36(m, 1H, —C=CH—), 6.26, 6.80(each d, J=11.5 Hz, each 1H, —C=CH—CH=C(CN)).

REFERENCE EXAMPLE 5

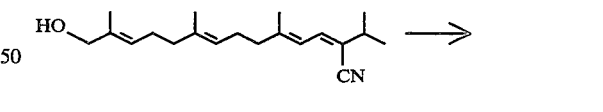

To the hydroxy compound obtained in Reference Example 4 in toluene (5 ml) was dropwise added a 1M solution of diisobutylaluminium hydride in toluene (2.0 ml, 2.0 mmol) at −70° C. under argon atmosphere. After two-hour-stirring at −70° C., a 1M aqueous solution of oxalic acid (4.0 ml) was added, and the mixture was allowed to warm gradually to room temperature with stirring under argon atmosphere. The organic layer was washed with water and saturated aqueous sodium bicarbonate, dried over Na$_2$SO$_4$, and evaporated in vacuo to remove the solvent. The resultant residue was purified with silica gel column chromatography (solvent: n-hexane/ethyl acetate=7:1) to obtain the aimed formyl compound.

IR(film)cm⁻¹; 3430, 2960, 2920, 2870, 1670, 1630, 1450, 1390, 1295, 1230, 1130, 1070, 1010.

₁H NMR(CDCl₃, 250 MHz )δppm; 1.04 (d, 6H, J=6.8 Hz, —CH(CH₃)₂) 1.59(d, J=0.6 Hz, 3H, CH₃—C≡), 1.63(brs, 3H, CH₃—C≡) , 1.86(d, J=1.2 Hz, 3H, CH₃—C≡), 1.7-2.2(m, 8H, —CH₂CH₂—), 2.88(hep.J=6.8 Hz, 1H, —CH(CH₃)₂), 3.95(brs, 2H, —CH₂OH), 5.09(m, 1H, —CH₂CH≡), 5.38(brt, J=6.8 Hz, 1H, —CH₂CH≡), 6.80(d, J=12.0 Hz, 1H, ≡CH—CH≡), 7.11(d, J=12.0 Hz, 1H, ≡CH—CH≡),10.25 (s, 1H, —CHO).

REFERENCE EXAMPLE 6

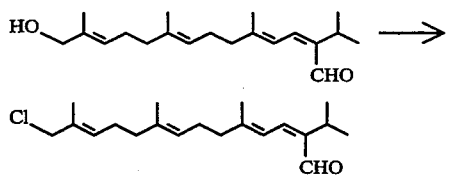

A solution of dry lithium chloride (64 mg, 1.5 mmol), 2, 6-lutidine (0.23 ml, 2.0 mmol) and hydroxy formyl compound (305 mg, 1.0 mmol) in dimethylformamide (1.0 ml) was chilled on an ice water bath and mixed with methanesulfonyl chloride (160 mg, 1.4 mmol) with stirring in argon atmosphere. About 8 hours later, the starting material was confirmed to disappear, and the reaction mixture was dissolved in water and ether. The organic layer was washed with water, dried over magnesium sulfate and concentrated. The residue was chromatographed on a column of silica gel eluting with n-hexane: ethyl acetate (15:1) as an eluent to give the objective chloroformyl compound (281 mg, 87%).

IR (film)cm⁻¹; 2970, 2930, 2880, 1670, 1630, 1445, 1390, 1295, 1265, 1135.

NMR (CDCl₃, 250 MHz)δppm; 1.04 (d, J=7.0 Hz, 6H, —CH(CH₃)₂), 1.59, 1.70 (each bs, each 3H, —C≡CCH₃), 1.87 (d, J=1.3 Hz, 3H, —C≡CCH₃), 1.9-2.2 (m, 8H, —CH₂CH₂—), 2.89 (hep, J=7.0 Hz, 1H, —CH(CH₃)₂), 3.98 (bs, 2H₂, —CH₂Cl), 5.09 (m, 1H, —C≡CHC H₂—), 5.47 (bt, J=6.5 Hz, 1H, —C≡CHCH₂—), 6.82 (d, J=12.0Hz, 1H, —C≡CH —CH≡C(CHO)—), 7.11 (d, J=12.0 Hz, —C≡CH—CH≡C(CHO)—), 10.27 (s, 1H, —CHO).

REFERENCE EXAMPLE 7

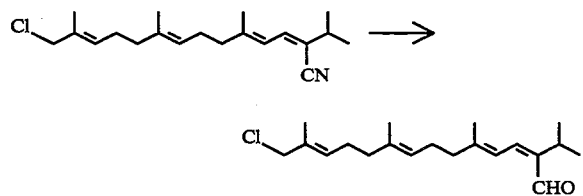

To a solution of the nitrile (14-chloro-2-(1-methylethyl)-5,9,13-trimethyl-2,4,8,12-tetradecatetraenenitril)(890 mg, 2.78 mmol) in n-hexane (30 ml) was dropwise added gradually a 1M solution (4.2 ml) of diisobutylaluminum hydride in toluene at −70° C. under argon atmosphere. One hour later, 2 ml of water was added to the mixture, and the bath was removed. The reaction mixture was vigorously stirred, and the resultant solid was filtered and washed with n-hexane.

The resultant filtrate was stirred still with 10% oxalic acid. The organic layer was washed, dried, filtered and concentrated. The residue was chromatographed on a column of silica gel eluting with n-hexane: ethyl acetate (20:2) to give the objective formyl compound (781 mg, 87%).

IR(film)cm⁻¹; 2970, 2930, 2880, 1670, 1630, 1445, 1390, 1295, 1265, 1135.

NMR(CDCl₃, 250 MHz)δppm; 1.04(d, J=7.0 Hz, 6H, —CH(CH₃)₂), 1.59, 1.70(each bs, each 3H, —C≡CCH₃), 1.87(d, J=1.3 Hz, 3H, —C≡CCH₃), 1.9-2.2(m, 8H, —CH₂CH₂—), 2.89 (hep, J=7.0 Hz, 1H, —CH(CH₃)₂), 3.98(bs, 2H, —CH₂Cl), 5.09 (m, 1H, —C≡CHCH₂—), 5.47(bt, J=6.5 Hz, 1H, —CH≡CHCH₂—), 6.82(d, J=12.0 Hz, 1H, —C≡ CH—CH≡C(CHO)—), 7.11(d, J=12.0 Hz, —C≡ CH—CH≡C(CHO)—), 10.27(s, 1H, —CHO).

REFERENCE EXAMPLE 8

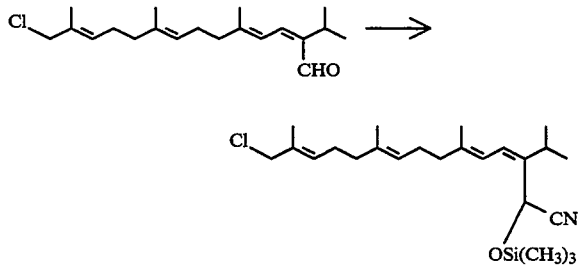

The-above formyl compound, 14-chloro-2-(1-methylethyl)-5,9,13-trimethyl-2,4,8,12-tetradecatetraenal (640 mg, 2.0 mmol) was dissolved in, trimethylsilylnitril (0.35 ml, 2.6 mmol). To the solution on an ice-water bath was added with stirring under argon atmosphere a trace amount of potassium cyanide/18-crown 6-ether complex. Two hours later, disappearance of the starting compound was confirmed. Excessive trimethylsilylnitrile was evaporated off to obtain crude 15-chloro-3-(1-methylethyl)-6,10,14-trimethyl-2-(trimethylsiloxy)-3,5,9,13pentadecatetraenenitrile (647 mg, quantitative).

IR(film)cm⁻¹; 2960, 2930, 2880, 2320, 1445, 1255, 1080, 875, 845.

NMR(CDCl₃, 250 MHz)δppm; 1.11, 1.15(each d, J=6.9 Hz, each 3H, —CH(CH₃)₂), 1.60, 1.71, 1.77(each s, each 3H, —C≡CCH₃), 1.9-2.2(m, 8H, —CH₂CH₂—), 2.64(hep, J=6.9 Hz, 1H, —CH(CH₃)₂, 3.99(s, 1H, —CH₂Cl) , 5.11(m, 1H, —C≡CHCH₂—), 5.33(s, 1H, —CHCN), 5.48(bt, J=6.5 Hz, 1H, —C≡CHCH₂—), 6.04, 6.25(each d, J=11.3 Hz, each 1H, —C≡ CH—CH≡C—).

REFERENCE EXAMPLE 9

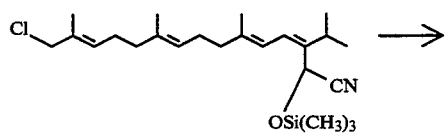

-continued

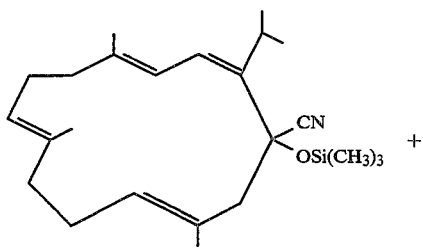

+

REFERENCE EXAMPLE 10

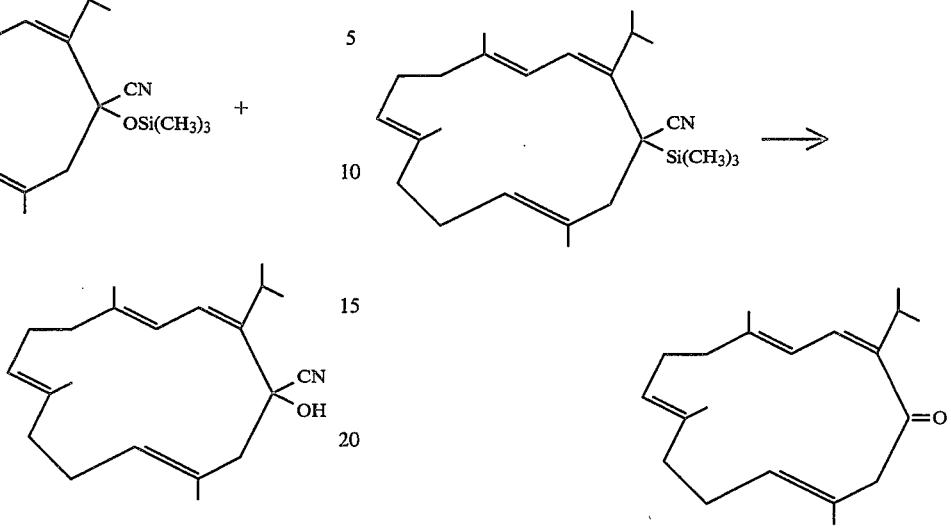

A solution of the crude cyanohydrine trimethylsilyl ether (647 mg, 2.00 mmol if it is 100% pure), which was obtained in Reference Example 8 in tetrahydrofuran (25 ml) was dropwise added with stirring at 50°–55° C. under argon atmosphere over 30 minutes to a solution of 1M lithium bis(trimethyisilyl)amide in tetrahydrofuran, which had been diluted with 25 ml of tetrahydrofuran. After completion of the dropwise addition, the tetrahydrofuran was evaporated off in vacuo, and the residue was dissolved in ethyl ether (30 ml), and the solution was walked with cooled 1N HCl, water, and then saturated aqueous sodium chloride. The organic layer was dried over MgSO4 and then concentrated to give a residue, which was then subjected to silica gel column chromatography (solvent: n-hexane/ethyl acetate=50:1–5:1) to obtain the aimed cyclized 2-(1-methylethyl)-5,9,13-trimethyl-1-trimethylsiloxy-2,4,8,12-cyclotetradecatetraen-1-carbonitrile (496 mg, 64%) and desilylated analogue (56 mg, 9%).

NMR spectrum of 1-trimethylsiloxy compound

NMR(CDCl3, 250 MHz)δppm; 0.23(s, 9H, —Si(CH3)3), 1.09, 1.15(each d, J=6.7 Hz, each 3H, —CH(CH3)2), 1.50, 1.62(each bs, each 3H, —C═CCH3), 1.70(d, J=1.3 Hz, 3H, —C═CCH3), 2.0–2.2(m, 8H, —CH2CH2—), 2.51(hep, J=6.7 Hz, 1H, —CH(CH3)2), 2.55, 2.65(each d, J=14.2 Hz, each 1H, —CHa Hb CN—), 4.94(bt, J=6.1 Hz, 1H, —C═CHCH2—), 5.15(bt, J=5.6 Hz, 1H, —C═CHCH2—), 6.17, 6.44(each d, J=11.8 Hz, each 1H, —C═CH—CH═C—).

NMR Spectrum of 1-hydroxy compound

NMR(CDCl3, 250 MHz)δppm; 1.15, 1.19(each d, J=6.7 Hz, each 3H, CH(CH3)2), 1.55, 1.63, 1.69(each s, each 3H, CH3—C═C—), 1.94–2.35(m, 8H, CH2—C═C—), 2.51(hep, J=6.7 Hz, 1H, CH(CH3)2), 2.66, 2.73(each d, J=14.1 Hz, 2H, CHa Hb CCN), 2.89(brs, 1H, OH), 4.93, 5.24(each brt, J=5.3 Hz, each 1H, —C═CH—CH2—), 6.22, 6.42(each d, J=11.1 Hz, each 1H, —C═CH—CH═C—).

The above cyanohydrine trimethylsilyl ether compound, 2-(1-methylethyl)-5,9,13-trimethyl-1-trimethylsiloxy-2,4,8,12-cyclotetradecatetraen-1-carbonitrile (657 mg, 1.7 mmol) was dissolved in 10% aqueous tetrahydrofuran (10 ml). To the solution on an ice-water bath was added a solution of 1M tetra n-butylammonium fluoride in tetrahydrofuran (0.02 ml), and the mixture was stirred and then allowed to stand at room temperature for 2 days. Most of the tetrahydrofuran was removed in vacuo and the residue was dissolved in ethyl ether. The ether layer was dried over MgSO4, filtered, concentrated, and subjected to silica gel column chromatography (solvent: n-hexane/ethyl acetate=30:1) to obtain the ketone compound, 2-(1-methylethyl)-5,9,13-trimethyl-2,4,8,12-cyclotetradecatetraen-1-one (411 mg, 85%).

REFERENCE EXAMPLE 11

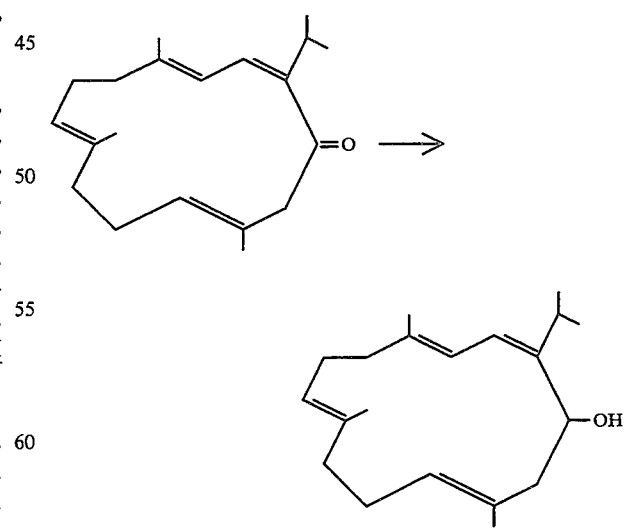

To the above ketone compound, 2-(1-methylethyl)-5,9,13-trimethyl-2,4,8,12-cyclotetradecatetraen-1-one (137 mg, 0.48 mmol) in dry toluene (2.5 ml) was dropwise added with stirring on a cooling bath at −70° C. a solution of 1M diisobutyl aluminium hydride in toluene (0.6 ml). One hour later, disappearance of the starting material was confirmed. After addition of water (0.25 ml) and removal of the cooling bath, the reaction mixture was stirred, followed by drying over MgSO4, filtration, and concentration to give a residue, which was subjected to silica gel column chromatography (solvent: n-hexane/ethyl acetate=12:1) to obtain the aimed sarcophytol A (125 mg, 88%).

REFERENCE EXAMPLE 12

Lithium aluminium hydride (80.0 mg, 2.11 mmol) was added to diethyl ether (5 ml) under argon atmosphere, and the mixture was stirred. To the suspension was dropwise added at room temperature over 5 minutes a solution of (1R,2S)-(−)-N-methylephedrine (308 mg, 2.12 mmol) in diethyl ether (5 ml). After one hour reflux of the reaction mixture with stirring, N-ethylaniline (0.53 ml, 4.23 mmol) was dropwise added thereto over 5 minutes, and the mixture was refluxed with stirring additional one hour. The mixture was then cooled to −72° C., and a solution of the ketone compound (136 mg, 0.475 mmol) obtained in Reference Example 10 in diethyl ether (3 ml) was gradually added thereto, and the mixture was stirred for 6 hours at −72° C. After addition of 1N HCl (9 ml), the organic layer was separated, washed with 3N HCl (5 ml×2), and dried over Na2SO4. Removal of the solvent in vacuo gave a residue, which was then subjected to silica gel column chromatography to give optically active sarcophytol A (81 mg, 60%) and nonreacted ketone compound (51 mg, 37%).

Optical purity of the optically active sarcophytol A was determined to be 87% by means of high pressure liquid chromatography using a separation column for optical isomers, specifically CHIRALCELL OD (commercially available from Daisel Kagaku Kogyo), said analysis being referred to as "HPLC analysis using CHIRALCELL OD" hereinafter.

REFERENCE EXAMPLE 13

A solution of lithium aluminum hydride in diethyl ether (2.26 ml, 1.40 mmol, 0.62M) was stirred under argon atmosphere. To the solution was dropwise added (S)-2-(anilinomethyl)pyrrolidine (296 mg, 1.68 mmol) in diethyl ether (3 ml) at room temperature over 10 minutes. The reaction mixture was stirred at room temperature additional one hour and then cooled to −72° C. To the mixture was gradually added the ketone compound (162 mg, 0.56 mmol)in diethyl ether (5 ml), which had been prepared in Reference Example 10. After one hour stirring at −72° C., saturated aqueous sodium bicarbonate (1 ml) was added, and the mixture was stirred at room temperature for 10 minutes. After addition of 1N HCl (15 ml) and diethyl ether (20 ml), the organic layer was separated. The aqueous layer was extracted with diethyl ether (20 ml), and the extract was washed with saturated aqueous sodium chloride (20 ml), dried over Na2SO4, and evaporated in vacuo to remove the solvent. The resultant residue was subjected to silica gel column chromatography to obtain optically active sarcophytol A (126 mg, 78%).

Optical purity of the thus obtained sarcophytol A was 92% when measured by HPLC analysis using CHIRALCELL OD. $[\alpha]^{24}_D$: +209.9° (c=0.372, CHCl3)

REFERENCE EXAMPLE 14

A solution of lithium aluminium hydride in diethyl ether (2.94 ml, 2.0 mmol, 0.68M) was stirred under argon atmosphere, and to the solution was gradually added (S)-2-(2,6-xylidinomethyl)pyrrolidine (490 mg, 2.4 mmol) at room temperature, and the mixture was stirred at room temperature for 2 hours. The reaction mixture was cooled to −74° C. and to the mixture was dropwise added over 10 minutes a solution of the ketone compound (69 mg, 0.24 mmol) in diethyl ether (3 ml), which had been prepared in Reference Example 10. After one hour stirring at −74° C., saturated aqueous sodium sulfonate (1 ml) was added, and the resultant mixture was stirred at room temperature for a while. After addition of diethyl ether (10 ml) and diluted HCl (20 ml), the organic layer was separated, and the aqueous layer was extracted with diethyl ether (20 ml). The extract was washed with saturated aqueous sodium chloride (20 ml), dried over Na2SO4, and evaporated in vacuo to remove the solvent to give a residue, which was subjected to silica gel column chromatography to obtain optically active sarcophytol A (61 mg, 88%).

Optical purity of the optically active sarcophytol A was 93% according to HPLC analysis using CHIRALCELL OD. $[\alpha]^{24}_D$:+204.4° (c=0.27, CHCl3)

REFERENCE EXAMPLE 15

A suspension of tin (II) chloride (382 mg, 2.01 mmol) and (R)-1-methyl-2-(piperidinomethyl)pyrrodine (366 mg, 2.01 mmol) in dichloromethane (6 ml) was cooled to −72° C. under argon atmosphere. To the suspension was added diisobutylaluminum hydride in toluene (1.0 mmol), and the mixture was stirred for ten minutes. To the mixture was gradually added at −72° C. a solution of the ketone compound (100 mg, 0.349 mmol) in dichloromethane (3 ml). The reaction mixture was stirred for 4 hours, and the stirring was continued at room temperature for 30 minutes after addition of saturated aqueous sodium chloride (3 ml). Resultant precipitates were filtered by the use of sellite, and the filtrate was dried over Na2SO4 and evaporated in vacuo to remove the solvent. The resultant residue was purified with silica gel column chromatography to give optically active sarcophytol A (79.2 mg, 79%).

Optical purity of the sarcophytol A thus obtained was 42% according to HPLC analysis using CHIRALCELL OD. $[\alpha]^{25}_D$:+101.9° (c=0.54, CHCl3)

INDUSTRIAL UTILITY

As stated above, the compounds (I) of the present invention are very useful as intermediates for preparing sarcophytol A which possesses an anti-carcinogenic promotor activity and anti-tumor activity. Thus, the present invention provides a method suitable for industrial production of sarcophytol A.

What is claimed is:

1. An acyclic terpene compound of the formula (I):

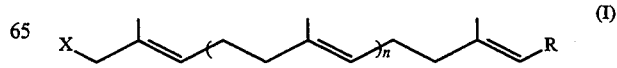

wherein R is a group of the formula:

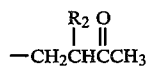

wherein $R^2$ is a hydrogen atom or $-CO_2R^3$; $R^3$ is a $C_1$–$C_4$ alkyl group; X is a group of the formula: $-OR^5$ wherein $R^5$ is a hydrogen atom, 1-alkoxyalkyl group, tetrahydrofuryl group or tetrahydropyranyl group, a silyl group substituted with a $C_1$–$C_5$ alkyl group or a phenyl group; and n is 0, with the proviso that when $R^5$ is a hydrogen atom, $R^2$ is not a hydrogen atom; and when $R^5$ is a 1-ethoxyethyl group, $R^3$ is not a methyl group.

* * * * *